United States Patent
Dai et al.

(10) Patent No.: US 10,806,877 B2
(45) Date of Patent: Oct. 20, 2020

(54) PORTABLE BREATHING MACHINE

(71) Applicant: MICOMME MEDICAL TECHNOLOGY DEVELOPMENT CO., LTD., Changsha, Hunan (CN)

(72) Inventors: Zheng Dai, Hunan (CN); Jin Ding, Hunan (CN); Wei Liu, Hunan (CN); Qinpeng Xu, Hunan (CN); Haoxuan Huang, Hunan (CN); Weili Li, Hunan (CN); Chao He, Hunan (CN); Menghang Lei, Hunan (CN); Xiaohui Zeng, Hunan (CN); Guangrong Wang, Hunan (CN)

(73) Assignee: MICOMME MEDICAL TECHNOLOGY DEVELOPMENT CO., LTD., Changsha, Hunan (CN)

( * ) Notice: Subject to any disclaimer, the term of this patent is extended or adjusted under 35 U.S.C. 154(b) by 492 days.

(21) Appl. No.: 15/561,066

(22) PCT Filed: Mar. 22, 2016

(86) PCT No.: PCT/CN2016/076991
§ 371 (c)(1),
(2) Date: Sep. 24, 2017

(87) PCT Pub. No.: WO2016/150373
PCT Pub. Date: Sep. 29, 2016

(65) Prior Publication Data
US 2018/0110944 A1    Apr. 26, 2018

(30) Foreign Application Priority Data

Mar. 24, 2015  (CN) .......................... 2015 1 0129278
Mar. 24, 2015  (CN) .......................... 2015 1 0129285
Mar. 24, 2015  (CN) .......................... 2015 1 0129347

(51) Int. Cl.
*A61M 16/00*   (2006.01)
*A61M 16/16*   (2006.01)
(Continued)

(52) U.S. Cl.
CPC ...... *A61M 16/0006* (2014.02); *A61M 16/022* (2017.08); *A61M 16/16* (2013.01);
(Continued)

(58) Field of Classification Search
CPC .......... A61M 16/0066; A61M 16/0006; A61M 16/022; A61M 2205/42; A61M 16/16;
(Continued)

(56) References Cited

U.S. PATENT DOCUMENTS 4,767,087 A * 8/1988 Combu ..................... F16L 3/11
                                                    248/324
6,322,247 B1 * 11/2001 Bonne ................... G01F 1/6842
                                                    374/138

(Continued)

FOREIGN PATENT DOCUMENTS

CN    103807221 A  *  5/2014  ............. F04D 17/16
EP    1191311 A2   *  3/2002  ................ G01F 1/40
GB    1599020 A    *  9/1981  ........... B32B 27/065

*Primary Examiner* — Kendra D Carter
*Assistant Examiner* — Thomas W Greig

(57) ABSTRACT

A portable breathing machine includes a body case (100), wherein: a fan box (101), a cut-off device (108) and a control device (113) are arranged in the body case (100); a fan (8) is arranged in the fan box (101) through a fan noise reduction device (102); an air outlet of the fan box (101) is connected with an internal breathing tube (107); the cut-off device (108) is arranged on the internal breathing tube (107); an air outlet of the cut-off device (108) is connected with an external breathing tube (104) and a mask (105); the fan noise reduction device (102) includes a lower flexible cover (3) and an upper flexible cover (5); the lower and upper flexible covers cooperate to form an enclosed cavity for containing the fan (8). A working noise of the breathing machine is decreased to below 15 decibel.

18 Claims, 10 Drawing Sheets

(51) Int. Cl.
*A61M 16/08* (2006.01)
*A61B 7/00* (2006.01)
*A61M 16/10* (2006.01)

(52) U.S. Cl.
CPC .......... *A61B 7/003* (2013.01); *A61M 16/0087* (2013.01); *A61M 16/0816* (2013.01); *A61M 16/1045* (2013.01); *A61M 16/161* (2014.02); *A61M 2016/0027* (2013.01); *A61M 2016/0036* (2013.01); *A61M 2205/42* (2013.01)

(58) Field of Classification Search
CPC ... G01F 1/00; G01F 1/002; G01F 1/07; G01F 1/206; G01F 1/34; G01F 1/36; G01F 1/40
See application file for complete search history.

(56) References Cited

U.S. PATENT DOCUMENTS

| | | | |
|---|---|---|---|
| 7,704,214 B2* | 4/2010 | Abraham-Fuchs | ........................... G01N 33/0037 600/532 |
| 7,878,980 B2* | 2/2011 | Ricciardelli | ........... A61B 5/091 600/529 |
| 2009/0007912 A1* | 1/2009 | Lindell | ................. A61M 16/10 128/204.18 |
| 2009/0071478 A1* | 3/2009 | Kalfon | .............. A61M 16/0051 128/204.17 |
| 2010/0245097 A1* | 9/2010 | Sung | ................. A61M 16/0066 340/627 |
| 2011/0180068 A1* | 7/2011 | Kenyon | ............ A61M 16/0875 128/203.26 |
| 2017/0049606 A1* | 2/2017 | Chen | ........................ A61F 5/566 |
| 2017/0292864 A1* | 10/2017 | Zhang | ....................... G01F 1/42 |

* cited by examiner

PORTABLE BREATHING MACHINE

CROSS REFERENCE OF RELATED APPLICATION

This is a U.S. National Stage under 35 U.S.C. 371 of the International Application PCT/CN2016/076991, filed Mar. 22, 2016, which claims priority under 35 U.S.C. 119(a-d) to CN 201510129285.3, CN 201510129347.0 and CN 201510129278.3, all filed Mar. 24, 2015.

BACKGROUND OF THE PRESENT INVENTION

Field of Invention

The present invention relates to a field of breathing machine, and more particularly to a portable breathing machine.

Description of Related Arts

The household sleep breathing machine is mainly applicable in personal home, sleep center and small clinic for patients having the apnea syndrome. The breathing machine is to pressurize the gas in the tube through the fan; and during the working process, it is inevitable for the fan to make a noise. Because the patients have the relatively low threshold tolerance of noise, the single and repeating stimulation generated by the noise leads that the patients cannot distinguish day and night. Thus, the noise of the breathing machine causes a greatly negative stimulation to the patients. How to control the noise in a smallest range for not influencing the sleep of the patients is an important issue that all the breathing machine manufacturers need to face.

The noise of the fan can be divided into two types. The first one is a wind howling sound generated by a friction between the blades and air due to a rapid rotation of the fan; the second one is a noise generated by a collision between the fan and other parts due to a shock caused by the own rotation and replacement of the fan. Generally, the latter is greatly larger than the former and is a main noise source.

In prior art, the conventional methods for controlling the noise of the fan have three types. For the first type, the fan is placed in a box which has a thick sound insulation material layer, wherein the sound insulation material is generally ethylene-vinyl acetate (EVA) material. However, the requirement on the sound insulation material is relatively high, and the box will generally have a relatively large volume, which is not beneficial to the cost control and the volume control of the breathing machine. Moreover, because the household breathing machine is mainly applied in the home and the sleep center, for convenience, the volume of the breathing machine is generally not large. For the second type, a sound insulation environment is generated through the air channel structure, which has a low cost, but has a greatly high requirement on the structure and thus is difficult to be realized. For the third type, the fan is fixed by increased rigid connection parts through the special protection treatment, which is able to reduce the noise generated by the shock of the fan. However, the problems of increased volume and increased cost still exist.

The Chinese patent publication, CN202010337U, discloses a noise reduction and shock absorption device for the breathing machine, wherein: the upper foam is fastened with the lower foam; a fan fixing groove is provided on the foam; the fan is fixed in an enclosed space formed by the upper and lower foam through the fan fixing groove. The vibration of the fan will transmit to the foam, so that the fan and the foam resonate together. A fan noise reduction structure is disclosed by Changzhou King Medical Co., Ltd. in the Chinese patent publication, CN103736186A, wherein: the fan body is tightly covered by the breathable soft layer and sealed in the airtight cabin together; the airtight cabin tightly contacts the breathable soft layer; the ventilation chambers are arranged at an upper part and a lower part of the airtight cabin. The fan body with the above fan noise reduction structure tightly contacts the airtight cabin through the breathable soft layer. As time goes, the breathable soft layer will harden, and the vibration of the fan body will transmit to the breathable soft layer and the airtight cabin, leading to the resonance.

The gas in the breathing machine is discharged from the fan air outlet after being pressurized by the fan. The gas has a certain flow velocity and pressure, which has the therapeutic effect on the patients. For better controlling the treatment condition and the patient condition, and providing the better convenience for the patients, the breathing machine is required to know the real-time gas pressure and flow velocity, wherein the real-time pressure and flow velocity is collected at the cut-off device. The cut-off device in the breathing machine is not only for collecting the data easily, but also for rectifying. The gas discharged by the fan is not stable, generally having the relative large turbulence. If the gas discharged by the fan is directly collected, the obtained data is not stable, which will have a great influence on the algorithms in software; and meanwhile, the patients will feel uncomfortable.

During the therapeutic process of the breathing machine, the pressurized gas will be continuously discharged from the fan. If the patients breathe with the mask for a long time, excessive drying is easily caused, and the patients will feel uncomfortable. If the weather becomes colder, the gas discharged by the breathing machine is cold air, and the patients are hard to accept the pressurized cold air. Moreover, the long-time use will make the patients easily catch a cold. Thus, it is necessary to process the gas discharged from the breathing machine with the heating and humidifying treatment. In most cases, a water storage box (hereinafter referred to as water box) is arranged at the air outlet of the breathing machine for containing a certain amount of water, and water in the water box is heated to achieve the heating and humidifying effect.

The breathing machine applicable in the hospital is operated by the specifically-assigned person and has a relatively wide operation environment, and thus the water box generally serves as an independent module. Considering the operation environment, the production cost and the operation convenience of the patients when at home and going out, the household breathing machine generally has a small volume and is portable. Thus, the water box of the household breathing machine is generally next to the main body of the breathing machine (as shown in FIG. 2); the water box is connected with the fan air outlet of the main body through the flexible sleeve and generally contains a certain amount of stored water therein. In order to avoid the water in the water box entering the main body when moving the breathing machine and avoid the main body being damaged, an anti-backflow structure is designed for the water box, so as to ensure that the stored water in the water box will not enter the main body through the tube or other pathways. Thus, how to design the anti-backflow structure for effectively avoiding the stored water in the water box entering the main body and damaging the main body is a problem required to be solved.

In prior art, the conventional methods for heating and humidifying the inlet gas of the breathing machines have two types. The first type is the active heating and humidifying device. The dry-cold air from the breathing machine flows through the water chamber before entering the lung of the patients, and is heated and humidified by the hot water in the water chamber. The second type is the passive heat and moisture exchanger which is made of the moisture absorption foam or paper. When passing through the passive heat and moisture exchanger, the gas of the breathing machine brings the moisture and the heat therein away. How to arrange a suitable water box structure which is able to select the above heating and humidifying device according to the air humidity is a difficult problem in the art.

SUMMARY OF THE PRESENT INVENTION

The existing problems in prior art are that a conventional breathing machine has a large noise, and water in a water box easily enters a main body of the breathing machine when moving the breathing machine, causing the main body being damaged.

An object of the present invention is to provide a low-noise breathing machine which is able to effectively reduce two noise sources of a fan, so as to solve the above existing problems in prior art.

The present invention is realized through following technical solutions.

A portable breathing machine comprises a body case, wherein: a fan box, a fan noise reduction device, a cut-off device and a control device are arranged in the body case; a fan is arranged in the fan box through the fan noise reduction device; an air outlet of the fan box is connected with an internal breathing tube; the cut-off device is arranged on the internal breathing tube; an air outlet of the cut-off device is connected with an external breathing tube and a mask; a lower flexible cover and an upper flexible cover of the fan noise reduction device cooperate with each other to form an enclosed cavity for containing the fan; and the fan hangs from the upper flexible cover through flexible hanging columns.

An enclosed S-shaped air channel and a fan air inlet channel which are successively connected are integrated at the fan noise reduction device.

An S-shaped air channel groove is provided at a bottom part of the lower flexible cover of the noise reduction device with fully utilizing space; and after assembling, the enclosed S-shaped air channel is formed between the lower flexible cover and the fan box.

The fan air inlet channel comprises a hole channel, an ascending channel and a descending channel, wherein: the ascending channel is formed by a through-hole which extends from bottom to top at the bottom part of the lower flexible cover; an exit of the ascending channel is located at an upper part of the enclosed cavity; the hole channel is provided at a bottom side wall of the through-hole and is interconnected with the enclosed S-shaped air channel and the ascending channel; the descending channel is formed from top to bottom around the fan in the enclosed cavity; after passing through the enclosed S-shaped air channel, gas passes through the hole channel at a tail end of the enclosed S-shaped air channel and enters the ascending channel, then gas reaches the upper part of the cavity after leaving from the exit of the ascending channel, and finally gas descends to a fan air inlet at a bottom part of the fan through the descending channel around the fan.

Preferably, the fan box comprises a bottom fan box and a top fan box, wherein: a bottom fan box damping piece is arranged between the bottom fan box and the lower flexible cover; and a top fan box damping piece is arranged between the top fan box and the upper flexible cover.

Preferably, an air channel structure further comprises a fan air outlet channel arranged at a fan air outlet, wherein: the fan air outlet channel comprises a flexible connection tube arranged at the fan air outlet; the flexible connection tube is connected with an elbow connection tube; and the elbow connection tube is connected with the internal breathing tube.

Preferably, a heating and humidifying device is arranged in the body case; the air outlet of the cut-off device is connected with the heating and humidifying device through the internal breathing tube; and an air outlet of the heating and humidifying device is connected with the external breathing tube and the mask.

Preferably, the enclosed S-shaped air channel and the fan air inlet channel are made through a mould before shaping the upper flexible cover and the lower flexible cover, and thereafter the upper flexible cover and the lower flexible cover are integrated together.

Preferably, at the bottom part of the lower flexible cover, with the fan as an original point, the enclosed S-shaped air channel is basically distributed in a first quadrant and a second quadrant, and an air inlet of the enclosed S-shaped air channel is arranged at a bottom of a side wall in the second quadrant of the lower flexible cover, where is directly opposite to an air inlet of the fan box.

Preferably, the enclosed S-shaped air channel at least comprises a first sinuous section and a straight section following a last sinuous section, which are successively connected; the first sinuous section is formed through firstly going straight from the air inlet for 40-60 mm at an angle of −90°, then going straight for 10-20 mm at an angle of 0°, and going straight for 40-60 mm at an angle of 90°; and the first sinuous section is connected with the straight section.

Preferably, the enclosed S-shaped air channel further comprises a second sinuous section, wherein: the second sinuous section is formed through going straight from a tail end of the first sinuous section for 10-20 mm at an angle of 0° and then going straight for 40-60 mm at an angle of −90°, plus a path of "going straight for 40-60 mm at an angle of 90°" of the first sinuous section; and a tail end of the second sinuous section is connected with the straight section.

Preferably, the enclosed S-shaped air channel further comprises a third sinuous section, wherein: the third sinuous section is formed through going straight from the tail end of the second sinuous section for 10-20 mm at an angle of 0° and then going straight for 40-60 mm at an angle of 90°, plus a path of "going straight for 40-60 mm at an angle of −90°" of the second sinuous section; and a tail end of the third sinuous section is connected with the straight section.

Preferably, the enclosed S-shaped air channel has a pathway of a smooth curve, wherein the smooth curve comprises at least two convex sections and a concave section.

Preferably, each flexible hanging column comprises a hanging column body and a flange which is arranged at an end of the hanging column body, wherein: a clamping groove is provided on the hanging column body; the flexible hanging column hangs from a hanging hole of the upper flexible cover through the flange; at least three clamping holes are provided on the fan; the fan is fixedly connected with the clamping grooves of the flexible hanging columns through the clamping holes; the clamping groove of each hanging column body is a thread groove; and the flexible hanging columns further fix the fan through a cooperation of flexible clamping nuts and the clamping grooves of the hanging column bodies.

Preferably, the lower flexible cover and the upper flexible cover are made of ethylene-vinyl acetate (EVA) material.

Preferably, each flexible hanging column comprises a metal reinforced frame, wherein: the metal reinforced frame is integrated with rubber and EVA material through injection molding.

Preferably, the cut-off device comprises a rectifying frame, a honeycomb rectifying part, a connection duct, a flexible sleeve, an external connection tube, a silica gel connection part and a sensor unit, wherein: the connection duct is a tubular part whose left end serves as an air inlet and right end serves as an air outlet; the air inlet is connected with the rectifying frame; the air outlet is inserted into a groove of the flexible sleeve; the external connection tube is inserted into an inner hole of the flexible sleeve; cut-off columns are arranged on the connection duct with an interval and have a certain distance from a center line; inner holes of the connection duct are respectively interconnected with inner holes of the cut-off columns; the cut-off columns of the connection duct are connected with the silica gel connection part; the silica gel connection part is connected with the sensor unit; and the honeycomb rectifying part is arranged between the connection duct and the rectifying frame.

Preferably, the cut-off columns comprise a first cut-off column, a second cut-off column and a third cut-off column, wherein: a first connection through-hole, a second connection through-hole and a third connection through-hole are provided on the silica gel connection part with a same interval as that of the cut-off columns; the sensor unit comprises a before-rectifying flow sensor, an after-rectifying flow sensor and an after-rectifying pressure sensor; air inlet ends of the first connection through-hole, the second connection through-hole and the third connection through-hole are respectively inserted into the corresponding first cut-off column, the second cut-off column and the third cut-off column of the connection duct; and the before-rectifying flow sensor, the after-rectifying flow sensor and the after-rectifying pressure sensor are respectively arranged at air outlet ends of the first connection through-hole, the second connection through-hole and the third connection through-hole.

Preferably, the rectifying frame comprises a cover body and a fastening part which is arranged inside the cover body, wherein: a top part of the cover body has an opening; a cross is arranged above the opening; an inner circumference surface of the cover body has a cover body connection part; a cut-off ring is arranged at an inner side of the air inlet of the connection duct; an inner fastening part is arranged on the cut-off ring; a connection part and an outer fastening part are arranged at an outer side of the air inlet of the connection duct; the honeycomb rectifying part has a plurality of honeycomb-shaped holes which are adjacent to each other, an upper end face fixing groove and a lower end face fixing groove thereon.

Preferably, an outer circumference surface of the honeycomb rectifying part cooperates with an inner circumference surface of the connection duct; the inner fastening part is fastened at a bottom part of the lower end face fixing groove; the cover body connection part of the rectifying frame is connected with the connection part of the connection duct; when the cover body connection part is fastened with the outer fastening part of the connection duct, the fastening part of the rectifying frame is inserted into and stopped at a bottom part of the upper end face fixing groove.

Preferably, the flexible sleeve is made of silica gel; the external connection tube comprises a fastening flange and a fastening head.

Preferably, the heating and humidifying device is formed through a cooperation of an upper cover and a bottom box, wherein: a bottom box flange is arranged in the bottom box for dividing the bottom box into a small chamber and a large chamber; an upper cover flange is arranged at the upper cover; when the upper cover cooperates with the bottom box, the upper cover flange is correspondingly cooperates with the bottom box flange; a through-hole is provided on the bottom box flange; a silica gel funnel sleeve is fixedly arranged at the through-hole through a rubber sealing part; the silica gel funnel sleeve comprises a small diameter section, a large diameter section and a conical transition section between the small diameter section and the large diameter section; a heat conduction plate is arranged in the middle of a lower end face of the bottom box; an air inlet is provided at a side of the small chamber; an air outlet is provided on the upper cover; the rubber sealing part comprises a hollow tube, and a first flange and a second flange are arranged around an end of the hollow tube; a distance between the first flange and the second flange cooperates with a thickness of the upper cover flange and the bottom box flange; an inner circular flange and an outer circular flange are arranged on the second flange with an interval; the large diameter section of the silica gel funnel sleeve is inserted into space between the inner circular flange and the outer circular flange; a smallest height from a center hole at the small diameter section of the silica gel funnel sleeve to the lower end face of the bottom box is large than a height from a max line to the lower end face of the bottom box by 10-20 mm.

Preferably, a U-shaped baffle is arranged at a lower end face of the upper cover, wherein: a U-shaped concave section of the U-shaped baffle is directly opposite to the small diameter section of the silica gel funnel sleeve; a silica gel air channel sleeve is arranged at the air inlet and is convex toward an interior of the small chamber by 15-30 mm; a waterproof rubber gasket is arranged on an upper end face of the bottom box and the bottom box flange; a passive heat and moisture exchanger (HME) is arranged above the small chamber; a pivot is arranged at the flange; a rotational switch valve is arranged at the pivot; and the upper cover flange has an opening thereon.

Preferably, the passive HME in parallel is arranged above the small chamber; the rotational switch valve which rotates around the pivot is arranged in the small chamber; and a middle side wall of the upper cover has an opening.

Preferably, the passive HME in series is arranged above the small chamber; an end of the silica gel air channel sleeve is connected to an exchanger air inlet through a flexible tube; an air inlet of the rubber sealing part is connected with an exchanger air outlet through a tube.

Preferably, the passive HME comprises an exchanger bottom plate, an exchanger top plate and a casing formed by exchanger side plates, wherein: the exchanger air inlet is provided on the exchanger bottom plate; the exchanger air outlet is provided on the exchanger top plate or the exchange bottom plate; an insulation plate is arranged between the exchanger bottom plate and the exchanger top plate; an HME material plate, a sealing insulation strip and an insulation heating plate are successively arranged on the insulation plate; a plurality of first air channel grooves, second air channel grooves and third air channel grooves are respectively provided on the HME material plate, the insulation strip and the insulation heating plate; the first air channel grooves, the second air channel grooves and the third air channel grooves are successively interconnected with each other; a water tank is arranged on the exchanger top plate and is directly opposite to the HME material plate; multiple lines of interconnection holes are provided at a bottom part of the water tank, which are directly opposite to protruding ribs among the first air channel grooves of the HME material plate.

Beneficial Effects of the Present Invention

The present invention solves the problem of noise reduction from the air channel structure combined with the fan noise reduction device through following technical solutions.

1) The S-shaped air channel is arranged at the fan air inlet; through at least three sinuous sections, the wind howling sound generated by the friction between the blades of the fan and air is effectively avoided.

2) The S-shaped air channel and the fan air inlet channel are integrated together and sealed in the fan box, so that noise is also controlled in the fan box, which further increases the noise reduction degree and facilitates assembling and maintaining. Meanwhile, through the enclosed S-shaped air channel, the external gas firstly passes through the upper part of the enclosed cavity and the descends to the fan air inlet at the bottom part of the fan; when passing through the enclosed cavity, the external gas brings the heat generated by the fan to the fan air outlet, thereby decreasing a temperature of the fan.

3) The fan air outlet is connected with the flexible connection tube, so that gas is transmitted to the patients freely and the noise generated by the collision between the fan air outlet and the external air channel due to the shock of the fan is avoided.

The above three improvements are distributed on the only air channel of air inlet and outlet of the fan. Although the improvements seem to be easy, the three improvements support each other on the noise reduction function, and a total noise reduction effect of combining the three improvements is larger than the sum of the effect of single improvement.

The noise reduction device of the present invention achieves the technical object of noise reduction through following technical solutions. Through the cooperation of flexible covering with flexible hanging, namely the cooperation of the hanging assembly with the upper and lower flexible covers, the transmission of the fan vibration is effectively avoided. The enclosed cavity formed by the upper flexible cover and the lower flexible cover provides a strengthened sound insulation environment for the fan which is arranged therein through the hanging assembly. Moreover, the upper flexible cover provides a flexible support for the hanging assembly and achieves the better vibration absorption effect. The flexible hanging and the flexible covering support each other functionally, and the total technical effect of the combination is better than the sum of the technical effects of the single flexible covering and the single flexible hanging.

With the above integrated noise reduction device and air channel structure, the low-noise breathing machine provided by the present invention is able to decrease the working noise to below 15 decibel.

The present invention solves the technical problem that how to accurately measure the pressure and the flow velocity from the fan air outlet channel of the breathing machine through the following technical solutions, namely through a cooperation of a flow stabilizing function of the cross with a flow rectifying function of the honeycomb rectifying part. The flow stabilizing function of the cross enables the airflow to become the laminar flow from the turbulent flow; and after passing through the honeycomb-shaped holes of the honeycomb rectifying part, the gas becomes the complete laminar condition; the laminar gas generates the certain pressure drop between the air inlet end and the air outlet end of the honeycomb rectifying part, so that the differential-pressure sensor obtains the current flow velocity of the gas. The primary rectification function of the cross and the secondary rectification function of the honeycomb rectifying part cooperate with each other functionally; and the total technical effect of the combination is large than the sum of the technical effects of the single cross and the single honeycomb rectifying part.

The anti-backflow structure provided by the present invention has following beneficial effects. The waterproof rubber gasket is arranged on the upper end face of the bottom box for sealing and preventing the water in the water box from flowing out of the water box during the operation process; the protruding part is arranged at the side edge of the bottom box, so that it is convenient to observe the water level in the water box during the operation process and is easy to control the water amount in the water box; the heat conduction plate is arranged at the lower end face of the bottom box, for heat conduction and insulation; during the operation process, the temperature of the heating plate is transmitted to the water box through the heat conduction plate, so as to heat the water in the water box; the smallest height from the center hole at the small diameter section of the silica gel funnel sleeve to the lower end face of the bottom box is larger than the height from the max line to the lower end face of the bottom box by 10-20 mm, so that when the water level is below the max line, no matter the position of the water box, water will not enter the silica gel funnel sleeve, thereby realizing the omnidirectional anti-backflow function. The above structure realizes the primary anti-backflow function of the present invention. The rubber sealing part covers the whole large diameter section of the silica gel funnel sleeve, so that even though a small amount of water enters the silica gel funnel sleeve, the water will not directly enter the small chamber, which assists the anti-backflow function. The first part of the silica gel air channel sleeve, which is convex toward the interior of the small chamber, avoids the water flowing into the main body of the breathing machine when a small amount of water enters the small chamber, and the above structure realizes the secondary anti-backflow function of the present invention. Meanwhile, the second part of the silica gel air channel sleeve, which is convex toward the exterior of the small chamber, is connected to the air outlet of the main body of the breathing machine, so that the gas discharged from the air outlet of the main body of the breathing machine will not be discharged sideways and all the gas enters the water box.

According to the present invention, the water box structure which automatically selects the heating and humidifying pathway according to the humidity of the inlet gas has following technical effects.

1) According to the air humidity, two humidifying pathways can be selected which have the different heating and humidifying effects. The first one is a pathway only from the passive HME to the air outlet; and the second one is a pathway only from space above the water in the large chamber of the water box to the air outlet.

2) The reinforced heating and humidifying structure which is realized through the series connection of the passive HME and the large chamber of the water box has an obvious effect and will make the patients having a good feeling in the upper respiratory tract.

The above anti-backflow structure design and the heating and humidifying structure design support each other functionally. Only when the anti-backflow function is realized, the heating and humidifying function can continuously play the role. The heating and humidifying structure tightly cooperates with the anti-backflow structure of the large and small chambers. The design of the large and small chambers is established based on the parallel connection or series connection of the passive HME and the large chamber of the water box. The structure of the water box provided by the present invention is obtained through the cooperation of the above two structure designs.

IN FIGURES

Figure 1:
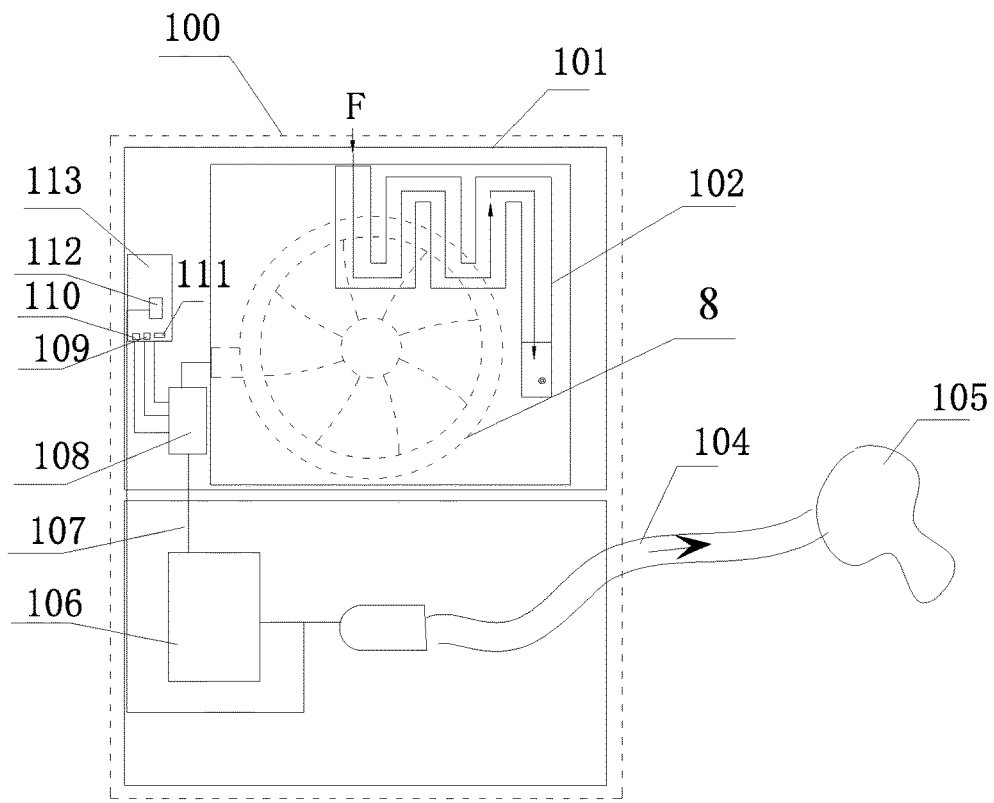
FIG. 1 is a connection sketch view of a breathing machine according to a preferred embodiment of the present invention.

100: body case; 101: fan box; 102: fan noise reduction device; 8: fan; 104: external breathing tube; 105: mask; 106: heating and humidifying device; 107: internal breathing tube; 108: cut-off device; 109: flow sensor; 110: pressure sensor; 111: flow velocity sensor; 112: temperature and humidity sensor; and 113: control device;

A': main body of breathing machine; and B': water box;

1: bottom fan box; 2: bottom fan box damping piece; 3: lower flexible cover; 4: top fan box; 5: upper flexible cover; 6: flexible hanging column; 7: top fan box damping piece; 8: fan; 9: flexible connection tube; 10: elbow connection tube; 11: fan air outlet; 12: fan air inlet; 13: hole channel; and F: external air;

3-1: enclosed S-shaped air channel; 3-1.1: first sinuous section; 3-1.2: second sinuous section; 3-1.3: third sinuous section; 3-1.4: straight section; 3-2: fan air inlet channel; 3-2.1: ascending channel; and 3-2.2: descending channel;

J-X: parts of cut-off device;

J-1: rectifying frame; J-2: honeycomb rectifying part; J-3: connection duct; J-4: flexible sleeve; J-5: external connection tube; J-6: silica gel connection part; and J-7: sensor unit;

J-1.1: cover body; J-1.2: fastening part; J-1.3: cross; and J-1.4: cover body connection part;

J-2.1: honeycomb-shaped hole; J-2.2: upper end face fixing groove; and J-2.3: lower end face fixing groove;

J-3.1: first cut-off column; J-3.2: second cut-off column; J-3.3: third cut-off column; J-3.4: cut-off ring; J-3.5: inner fastening part; J-3.6: outer fastening part; J-3.7: connection part; J-3.8: first locating column; and J-3.9: second locating column;

J-5.1: fastening flange; and J-5.2: fastening head;

J-6.1: first connection through-hole; J-6.2: second connection through-hole; and J-6.3: third connection through-hole;

J-7.1: before-rectifying flow sensor; J-7.2: after-rectifying flow sensor; and J-7.3: after-rectifying pressure sensor;

W-X: parts of water box;

W-1: upper cover; W-1.1: air outlet; and W-1.2: U-shaped baffle;

W-2: waterproof rubber gasket;

W-3: bottom box; W-3.1: air inlet; W-3.2: small chamber; W-3.3: large chamber; W-3.4: heat conduction plate; W-3.5: silica gel air channel sleeve; and W-3.6: protruding part;

W-4: silica gel funnel sleeve; W-4.1: small diameter section; W-4.2: conical transition section; W-4.3: large diameter section; W-5: rubber sealing part; W-5.1: first flange; W-5.2: second flange; W-5.3: inner circular flange; W-5.4: outer circular flange; W-6: opening; W-7: rotational switch valve; and W-8: passive HME;

801: exchanger air inlet; 802: insulation plate; 803: HME material plate; 803-1: first air channel groove; 804: sealing insulation strip; 804-1: second air channel groove; 805: insulation heating plate; 805-1: third air channel groove; 806: exchanger air outlet; 807: exchanger bottom plate; 808: exchanger top plate; 809: exchanger side plate; 810: water tank; 811: interconnection hole; and F': dry-cold air.

DETAILED DESCRIPTION OF THE PREFERRED EMBODIMENT

The following preferred embodiment is for illustrating the present invention, but not for limiting the scope of the present invention.

As shown in FIG. 1, according to a preferred embodiment of the present invention, a low-noise breathing machine comprises a body case 100, wherein: an air inlet of the breathing machine is arranged at the body case 100; a fan box 101, a fan noise reduction device 102, a cut-off device 108, a heating and humidifying device 106 and a control device 113 are arranged in the body case 100; a fan 8 is arranged in the fan box 101 through the fan noise reduction device 102; an air outlet of the fan box 101 is connected with an internal breathing tube 107; the cut-off device 108 is arranged on the internal breathing tube 107; a flow sensor 109, a pressure sensor 110 and a flow velocity sensor 111 are arranged in the cut-off device 108; the flow sensor 109, the pressure sensor 110 and the flow velocity sensor 111 are all connected with the control device 113; an air outlet of the cut-off device 108 is connected with the heating and humidifying device 106 through the internal breathing tube 107; an air outlet of the heating and humidifying device is connected with an external breathing tube 104 and a mask 105; and the heating and humidifying device 106 is improved.

Figure 2:
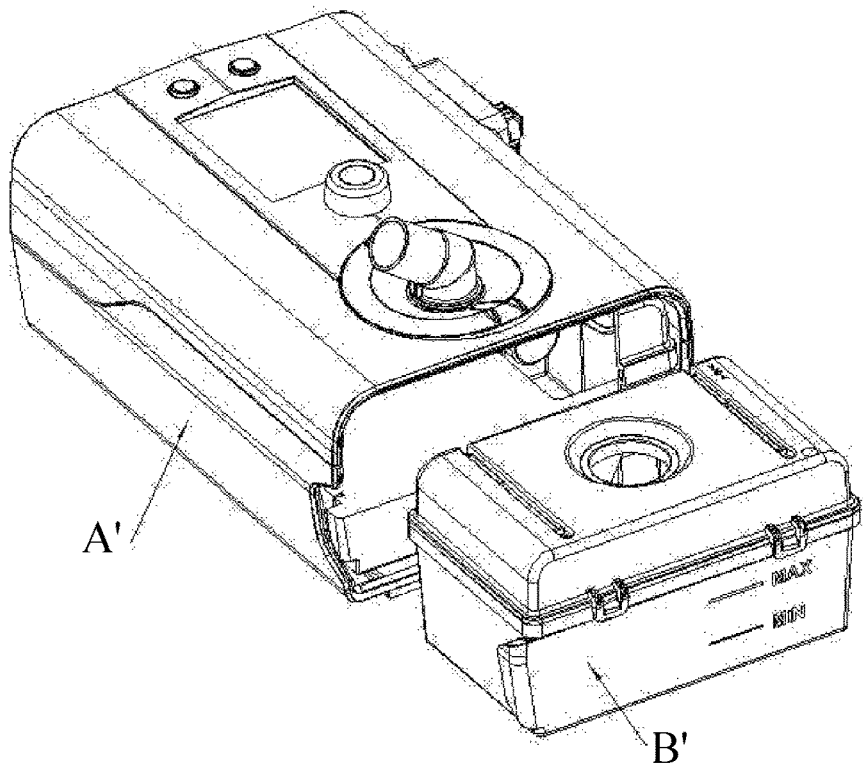
FIG. 2 is an axonometric drawing of the breathing machine according to the preferred embodiment of the present invention.
Figure 3:
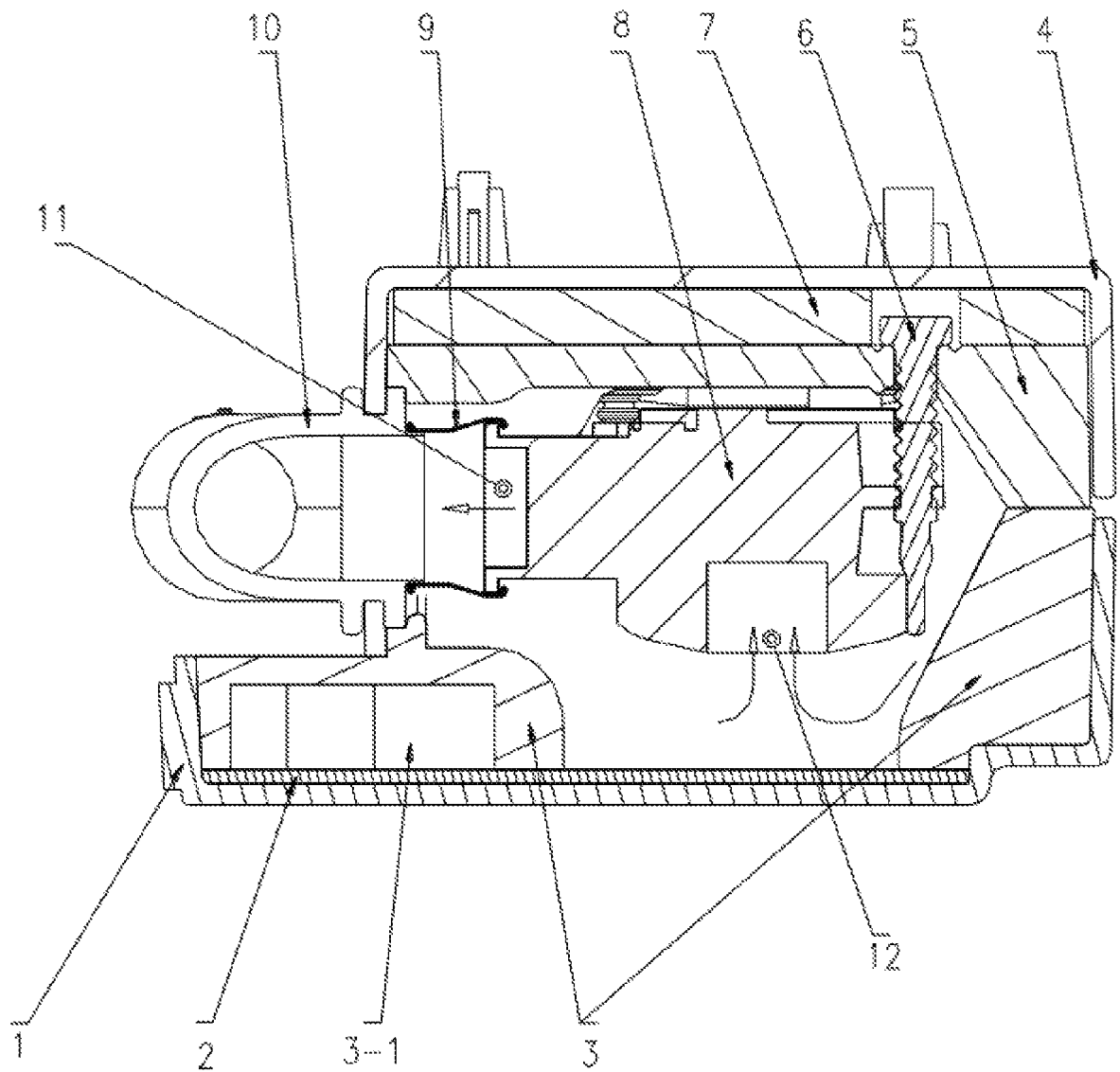
FIG. 3 is a structural sketch view of a fan noise reduction device of the breathing machine according to the preferred embodiment of the present invention.

As shown in FIGS. 2-3, the fan noise reduction device 102 comprises a lower flexible cover 3, an upper flexible cover 5, a bottom fan box damping piece 2 and a top fan box damping piece 7, wherein: the bottom fan box damping piece 2 is arranged on a bottom fan box 1; the top fan box damping piece 7 is arranged below a top fan box 4; the lower flexible cover 3 is arranged on the bottom fan box damping piece 2; the upper flexible cover 5 is arranged below the top fan box damping piece 7; the lower flexible cover 3 cooperates with the upper flexible cover 5 to form an enclosed cavity for containing the fan 8; at least three hanging holes are provided on the upper flexible cover 5; a flexible hanging column 6 is arranged in each hanging hole; the fan 8 hangs from the flexible hanging columns 6; and, the upper flexible cover 5 and the lower flexible cover 3 provide external gas and a temperature reduction function for the fan 8.

With fully utilizing space, an air channel structure is arranged at a bottom part of the lower flexible cover 3 of the fan noise reduction device 102, wherein: the air channel structure comprises an enclosed S-shaped air channel 3-1 and a fan air inlet channel 3-2 which are successively connected and arranged at a fan air inlet 12; and the air channel structure further comprises a fan air outlet channel arranged at a fan air outlet 11, as shown in FIGS. 2-3.

Figure 4:
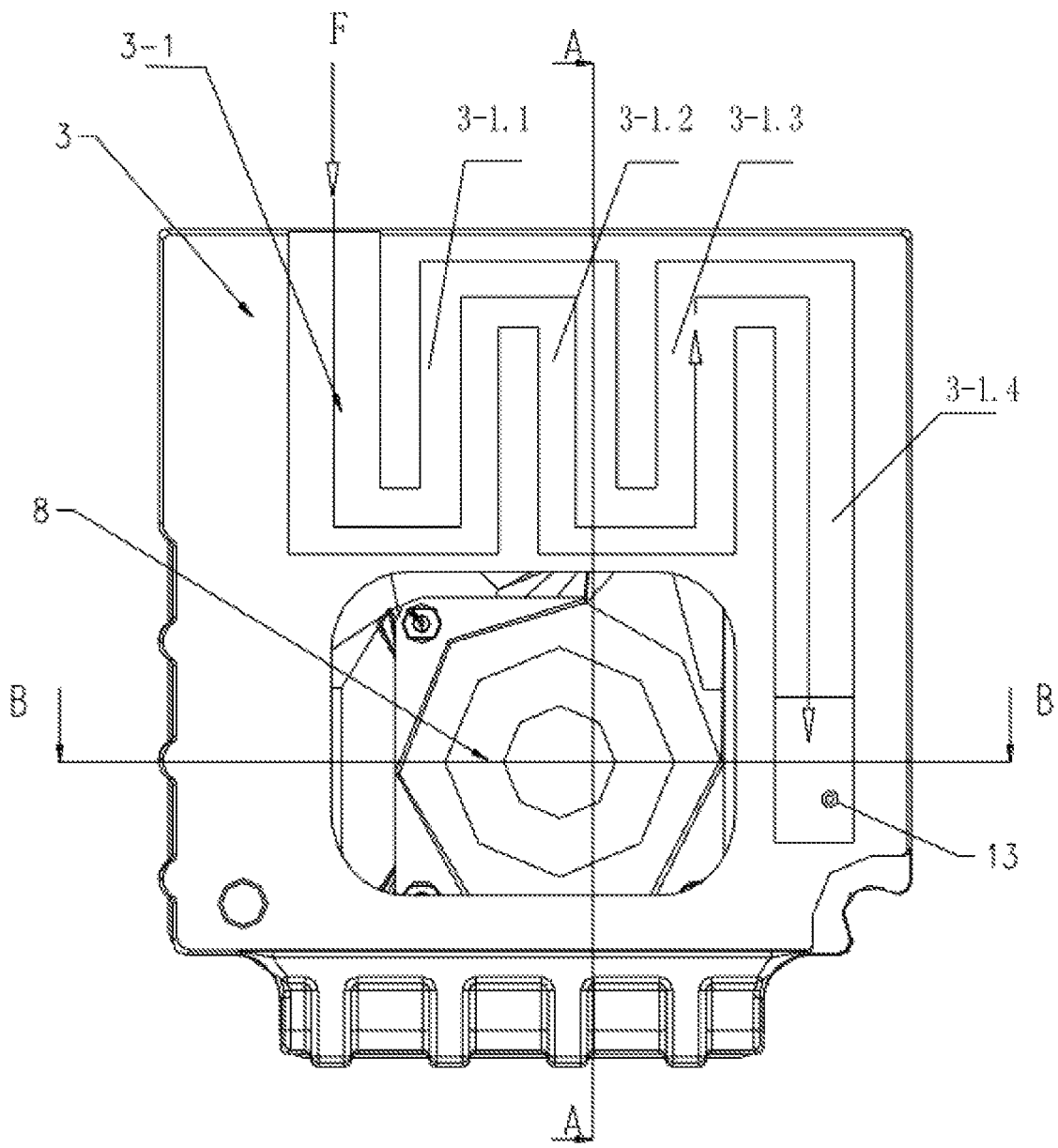
FIG. 4 is a sketch view of an air channel structure of the breathing machine according to the preferred embodiment of the present invention.

As shown in FIG. 4, the air channel structure comprises the enclosed S-shaped air channel 3-1, the fan air inlet channel 3-2 and the fan air outlet channel.

The enclosed S-shaped air channel 3-1 is described as follows. An S-shaped air channel groove is provided at the bottom part of the lower flexible cover 3 with fully utilizing space. After assembling, the enclosed S-shaped air channel 3-1 is formed between the lower flexible cover 3 and the bottom fan box damping piece 2; the enclosed S-shaped air channel 3-1 at least comprises a first sinuous section 3-1.1 and a straight section 3-1.4 following a last sinuous section, which are successively connected; at the bottom part of the lower flexible cover, with the fan as an original point, the enclosed S-shaped air channel 3-1 is distributed in a first quadrant and a second quadrant; an air inlet of the enclosed S-shaped air channel is arranged at a bottom of a first side wall in the second quadrant of the lower flexible cover 3, where is directly opposite to an air inlet of the fan box 101; the enclosed S-shaped air channel 3-1 starts from the air inlet, and then the first sinuous section 3-1.1 is formed through firstly going straight from the air inlet for 40-60 mm at an angle of −90°, then going straight for 10-20 mm at an angle of 0°, and going straight for 40-60 mm at an angle of 90°.

A second sinuous section 3-1.2 is formed through going straight from the first sinuous section for 10-20 mm at an angle of 0° and then going straight for 40-60 mm at an angle of −90°, plus a path of "going straight for 40-60 mm at an angle of 90°" of the first sinuous section.

A third sinuous section 3-1.3 is formed through going straight from the second sinuous section for 10-20 mm at an angle of 0° and then going straight for 40-60 mm at an angle of 90°, plus a path of "going straight for 40-60 mm at an angle of −90°" of the second sinuous section.

Through at least one sinuous section, the air channel structure reaches a second side wall of the lower flexible cover 3 without penetrating through the lower flexible cover, then goes straight at an angle of −90° along the straight section 3-1.4 having a length equal to the whole second side wall of the lower flexible cover 3, thereafter upwards passes through a hole channel 13 at a tail end of the enclosed S-shaped air channel 3-1 and passes through the lower flexible cover 3, and finally enters an upper part of the cavity, as shown in FIGS. 2-3.

The enclosed S-shaped air channel 3-1 comprises at least one sinuous section. Preferably, the enclosed S-shaped air channel 3-1 comprises at least one sinuous section with a pathway of a smooth curve.

Figure 5:
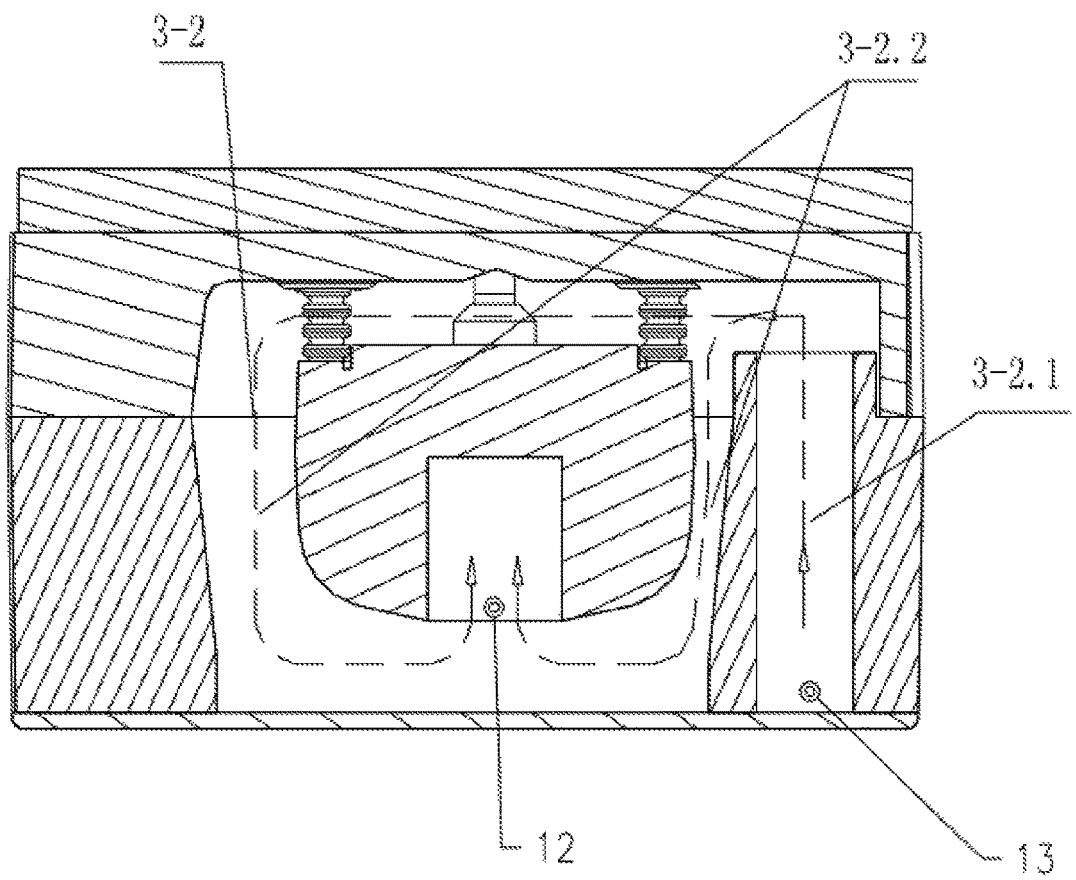
FIG. 5 is a B-B sectional view of the fan noise reduction device shown in FIG. 3.
Figure 6:
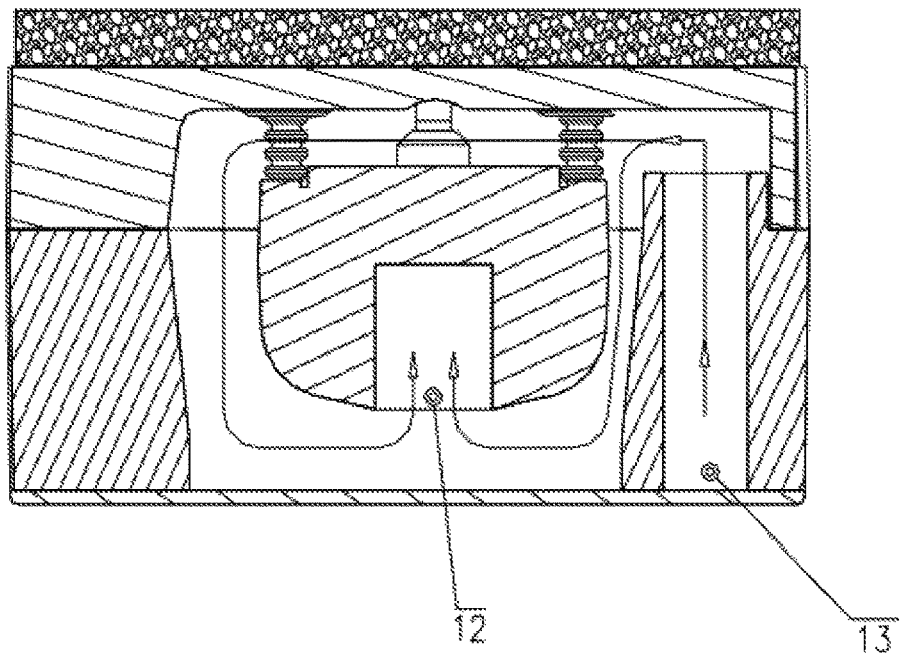
FIG. 6 is an A-A sectional view of the fan noise reduction device shown in FIG. 3.

As shown in FIGS. 5-6, the fan air inlet channel 3-2 comprises the hole channel 13, an ascending channel 3-2.1 and a descending channel 3-2.2, wherein: the ascending channel 3-2.1 is formed by a through-hole which extends from bottom to top at the bottom part of the lower flexible cover 3; the hole channel 13 is provided at a bottom side wall of the through-hole; the hole channel 13 is interconnected with the enclosed S-shaped air channel 3-1 and the ascending channel 3-2.1; the descending channel 3-2.2 is formed from top to bottom around the fan 8 in the enclosed cavity; after passing through the enclosed S-shaped air channel 3-1, gas passes through the hole channel 13 at the tail end of the enclosed S-shaped air channel 3-1 and enters the ascending channel 3-2.1, then gas reaches the upper part of the cavity after leaving from an exit of the ascending channel 3-2.1, and finally gas descends to the fan air inlet 12 at a bottom part of the fan 8 through the descending channel 3-2.2 around the fan 8.

The fan air outlet channel comprises a flexible connection tube 9 which is arranged at the fan air outlet 11 and has a length of about 3 cm, wherein: the flexible connection tube 9 is connected with an elbow connection tube 10; the elbow connection tube 10 is connected with an air channel outside the fan box 101, so that noise generated by a collision between the fan air outlet 11 and an external air channel due to a shock of the fan is avoided, as shown in FIG. 1 and FIG. 3.

The enclosed S-shaped air channel 3-1 having a relatively long and sinuous pathway is able to effectively reduce a wind howling sound generated by a friction between the fan air inlet 12 and air, and meanwhile avoid a wind howling sound generated by a friction between blades of the fan and air. Moreover, external air F enters the enclosed S-shaped air channel 3-1 formed by the lower flexible cover 3 and the bottom fan box damping piece 2 through the air inlet of the enclosed S-shaped air channel, then enters the upper part of the cavity and descends to the fan air inlet 12 at the bottom part of the fan 8, and finally is discharged out through the fan air outlet 11. When passing through the enclosed cavity, the external air F brings heat generated by the fan 8 to the fan air outlet 11, and then the heat is discharged out of the fan box 101 with the external air, thereby decreasing a temperature of the fan.

Preferably, in order to save cost and increase a noise reduction effect, according to the preferred embodiment of the present invention, the enclosed S-shaped air channel 3-1 is integrated with the fan air inlet channel 3-2. After passing through the enclosed S-shaped air channel 3-1, gas directly enters the fan air inlet channel 3-2, and then is pressurized by the fan 8 and discharged out. The above structure has following beneficial effects. On the one hand, a distance between the fan air inlet 12 and the fan 8 is decreased. If the distance is too long, an air inflow will become small; in order to guarantee a certain pressure output, a motor has to increase power, which increases a risk of burnout. On the other hand, through integrating the enclosed S-shaped air channel 3-1 with the fan air inlet channel 3-2, it is convenient to seal the whole air channel structure in the fan box 101, which further increases a noise reduction degree and facilitates assembling and maintaining. According to the present invention, the fan box 101 is composed of an upper part and a lower part, and an interior of the fan box is filled with a flexible material, wherein: the flexible material is preferred to be ethylene-vinyl acetate (EVA) material; the flexible material is composed of an upper part and a lower part which just fit the fan box; before shaping of the flexible material, the enclosed S-shaped air channel 3-1 and the fan air inlet channel 3-2 are made, and then the upper part and the lower part of the flexible material are integrated together, as shown in FIG. 4.

Preferably, in order to achieve a better noise reduction effect, according to the present invention, the sinuous air channel structure is made of the EVA material. The EVA material is a soft material reaching a medical standard, which not only has a noise reduction function but also has a certain filtration function, so that gas transmitted to the patients has less bacteria and dust. Moreover, the EVA material has a certain insulation effect on noise generated by a rotation of the fan, which reduces the noise heard by the patients.

The present invention solves the problem of noise reduction from the air channel structure through following technical solutions.

1) The S-shaped air channel is arranged at the fan air inlet; through at least three sinuous sections, the wind howling sound generated by the friction between the fan air inlet and air is effectively reduced, and meanwhile the wind howling sound generated by the friction between the blades of the fan and air is avoided.

2) The S-shaped air channel and the fan air inlet channel are integrated together and sealed in the fan box, so that noise is also controlled in the fan box, which further increases the noise reduction degree and facilitates assembling and maintaining.

3) The fan air outlet is connected with the flexible connection tube, so that gas is transmitted to the patients freely and the noise generated by the collision between the fan air outlet and the external air channel due to the shock of the fan is avoided.

The above three improvements are distributed on the only air channel of air inlet and outlet of the fan. Although the improvements seem to be easy, the three improvements support each other on the noise reduction function, and a total noise reduction effect of combining the three improvements is larger than the sum of the effect of single improvement.

Figure 7:
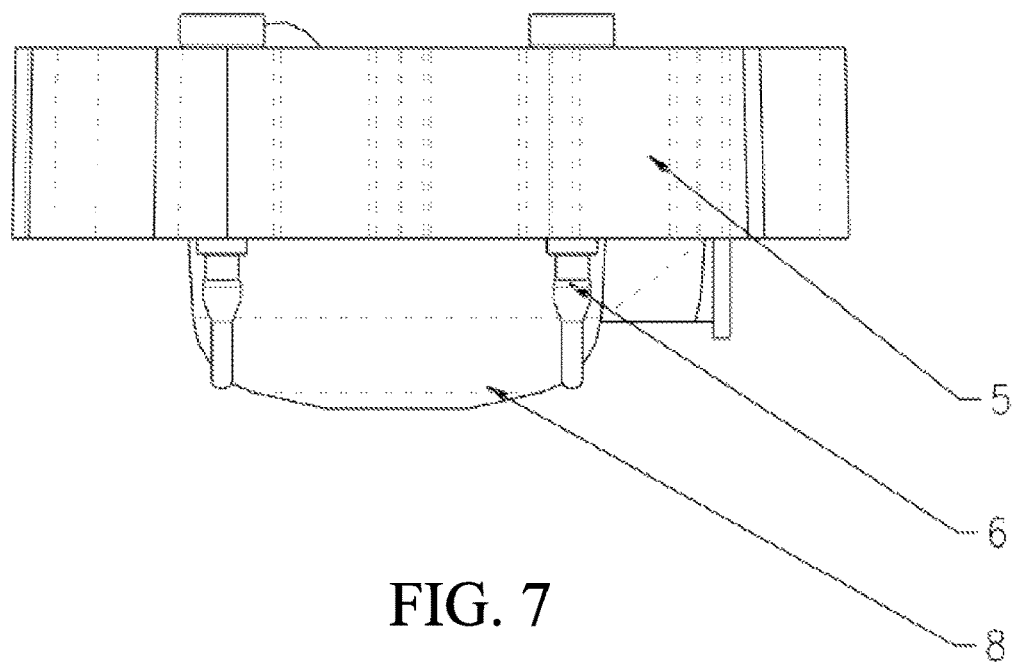
FIG. 7 is a front view of a flexible hanging column of the fan noise reduction device according to the preferred embodiment of the present invention.
Figure 8:
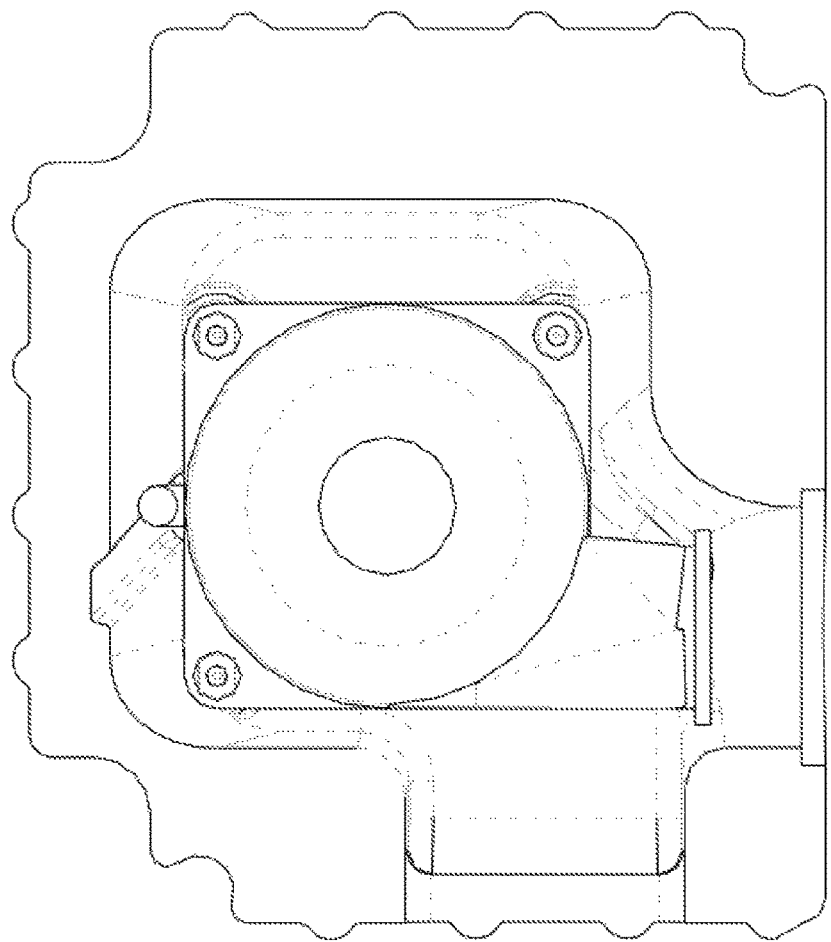
FIG. 8 is a top view of the flexible hanging column of the fan noise reduction device according to the preferred embodiment of the present invention.

As shown in FIGS. 7-8, each flexible hanging column 6 comprises a hanging column body and a flange which is arranged at an end of the hanging column body, wherein: a clamping groove is provided on the hanging column body; the flexible hanging column 6 hangs from the hanging hole of the upper flexible cover 5 through the flange; at least three clamping holes are provided on the fan 8; the fan 8 is fixedly connected with the clamping grooves of the flexible hanging columns 6 through the clamping holes; the clamping groove of each hanging column body is a thread groove; and the flexible hanging columns 6 further fix the fan 8 through a cooperation of flexible clamping nuts and the clamping grooves of the hanging column bodies.

Figure 9:
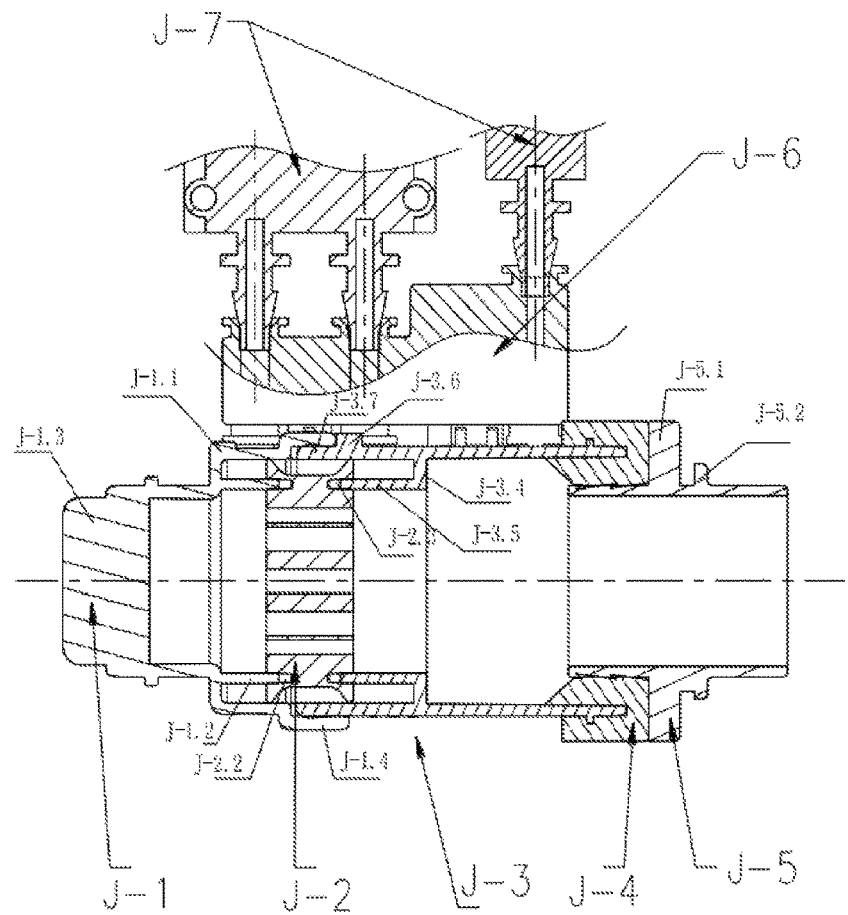
FIG. 9 is a main sectional view of a cut-off device according to the preferred embodiment of the present invention.
Figure 10:
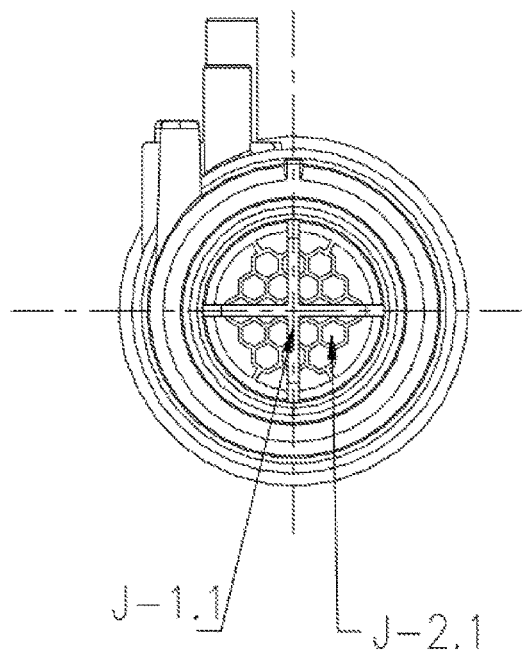
FIG. 10 is a left view of the cut-off device according to the preferred embodiment of the present invention.
Figure 11:
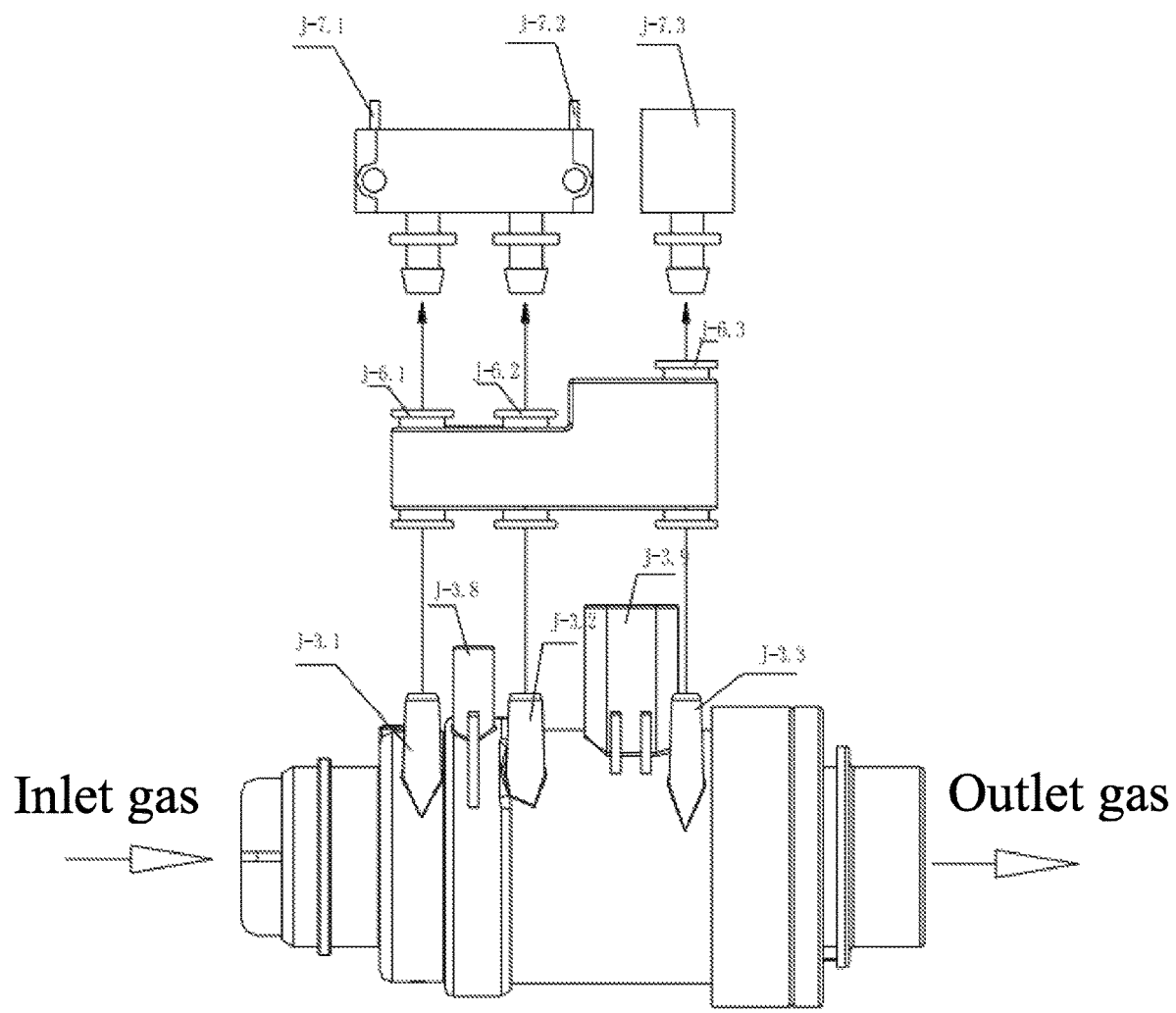
FIG. 11 is an exploded view of the cut-off device according to the preferred embodiment of the present invention.

As shown in FIGS. 9-11, the cut-off device 108 provided by the present invention is realized as follows. The cut-off device 108 comprises a connection duct J-3, wherein: the connection duct J-3 is a tubular part whose left end serves as an air inlet and right end serves as an air outlet; the air inlet is connected with a rectifying frame J-1, and the air outlet is inserted into a groove of a flexible sleeve J-4; an external connection tube J-5 is inserted into an inner hole of the flexible sleeve J-4; a silica gel connection part J-6 is connected with the connection duct J-3; the silica gel connection part J-6 is connected with a sensor unit J-7; and a honeycomb rectifying part J-2 is arranged between the connection duct J-3 and the rectifying frame J-1.

A first cut-off column J-3.1, a second cut-off column J-3.2 and a third cut-off column J-3.3 are arranged on the connection duct J-3 with an interval and have a certain distance from a center line; inner holes of the connection duct J-3 are respectively interconnected with inner holes of the first cut-off column J-3.1, the second cut-off column J-3.2 and the third cut-off column J-3.3. A cut-off ring J-3.4 is arranged at an inner side of the air inlet of the connection duct J-3; an inner fastening part J-3.5 is arranged on the cut-off ring J-3.4; and a connection part J-3.7 and an outer fastening part J-3.6 are arranged at an outer side of the air inlet. The connection duct J-3 further comprises a first locating column J-3.8 and a second locating column J-3.9, which are for locating and supporting a circuit board.

The silica gel connection part J-6 has a first connection through-hole J-6.1, a second connection through-hole J-6.2 and a third connection through-hole J-6.3 thereon with a same interval as that of the cut-off columns, J-3.1, J-3.2 and J-3.3. Air inlet ends of the first connection through-hole J-6.1, the second connection through-hole J-6.2 and the third connection through-hole J-6.3 are respectively inserted into the corresponding first cut-off column J-3.1, second cut-off column J-3.2 and third cut-off column J-3.3 of the connection duct J-3. A before-rectifying flow sensor J-7.1, an after-rectifying flow sensor J-7.2 and an after-rectifying pressure sensor J-7.3 are respectively arranged at air outlet ends of the first connection through-hole J-6.1, the second connection through-hole J-6.2 and the third connection through-hole J-6.3.

The rectifying frame J-1 comprises a cover body J-1.1 and a fastening part J-1.2 which is arranged inside the cover body, wherein: a top part of the cover body has an opening; a cross J-1.3 is arranged above the opening; and an inner circumference surface of the cover body has a cover body connection part J-1.4.

The honeycomb rectifying part J-2 has a plurality of honeycomb-shaped holes J-2.1 which are adjacent to each other, an upper end face fixing groove J-2.2 and a lower end face fixing groove J-2.3 thereon; the honeycomb rectifying part J-2 has functions of rectifying and collecting airflow data; an outer circumference surface of the honeycomb rectifying part J-2 cooperates with an inner circumference surface of the connection duct J-3; the inner fastening part J-3.5 is fastened at a bottom part of the lower end face fixing groove J-2.3; the cover body connection part J-1.4 of the rectifying frame J-1 is connected with the connection part J-3.7 of the connection duct J-3; when the cover body connection part J-1.4 is fastened with the outer fastening part J-3.6 of the connection duct J-3, the fastening part J-1.2 of the rectifying frame J-1 is inserted into and stopped at a bottom part of the upper end face fixing groove J-2.2.

The flexible sleeve J-4 is made of silica gel. The external connection tube J-5 comprises a fastening flange J-5.1 and a fastening head J-5.2.

The rectifying frame J-1 is connected with the air inlet of the connection duct J-3 through threaded connection, clamping or ultrasonic welding. An interference fit exists between the groove of the flexible sleeve J-4 and the air outlet of the connection duct J-3. Through an interference fit, an air inlet end of the external connection tube J-5 is inserted into the inner hole of the flexible sleeve J-4 and stopped by the fastening flange J-5.1; because of sealing performance of the silica gel, no air leakage occurs and airflow is smooth.

After reaching the cut-off device 108 through the fan air outlet 11, the airflow firstly passes through the rectifying frame J-1, wherein: the cross J-1.3 of the rectifying frame 1 is able to stabilize gas without affecting a forward flowing process of the gas; if adopting other forms, the rectifying effect will not be achieved. The rectifying frame J-1 is connected with the air inlet of the connection duct J-3, the cross J-1.3 is arranged inside an upstream air channel, and the cover body J-1.1 is arranged outside the upstream air channel, so as to achieve a best rectifying effect; if a distance of the cross J-1.3 is too long or too short, the rectifying effect cannot be achieved, which influences the therapeutic effect. After being stabilized by the rectifying frame J-1, the gas passes through the honeycomb rectifying part J-2 which is a circular plastic part having the honeycomb-shaped holes, has a secondary rectifying effect on the gas, and is able to form a differential pressure. When the gas passes through the honeycomb rectifying frame J-2, a pressure drop is generated between an air inlet end and an air outlet end of the honeycomb rectifying part J-2; through the pressure drop, a differential-pressure sensor is able to obtain a current flow velocity of the gas.

The present invention solves a technical problem that how to measure the pressure and the flow velocity from the fan air outlet channel of the breathing machine through following technical solutions, namely through a cooperation of a flow stabilizing function of the cross J-1.3 with a flow rectifying function of the honeycomb rectifying part J-2. The flow stabilizing function of the cross enables the airflow to become the laminar flow from the turbulent flow; and after passing through the honeycomb-shaped holes of the honeycomb rectifying part J-2, the gas becomes the complete laminar condition; the laminar gas generates the certain pressure drop between the air inlet end and the air outlet end of the honeycomb rectifying part, so that the differential-pressure sensor obtains the current flow velocity of the gas. The primary rectification function of the cross J-1.3 and the secondary rectification function of the honeycomb rectifying part J-2 cooperate with each other functionally; and the total technical effect of the combination is large than the sum of the technical effects of the single cross and the single honeycomb rectifying part.

Figure 12:
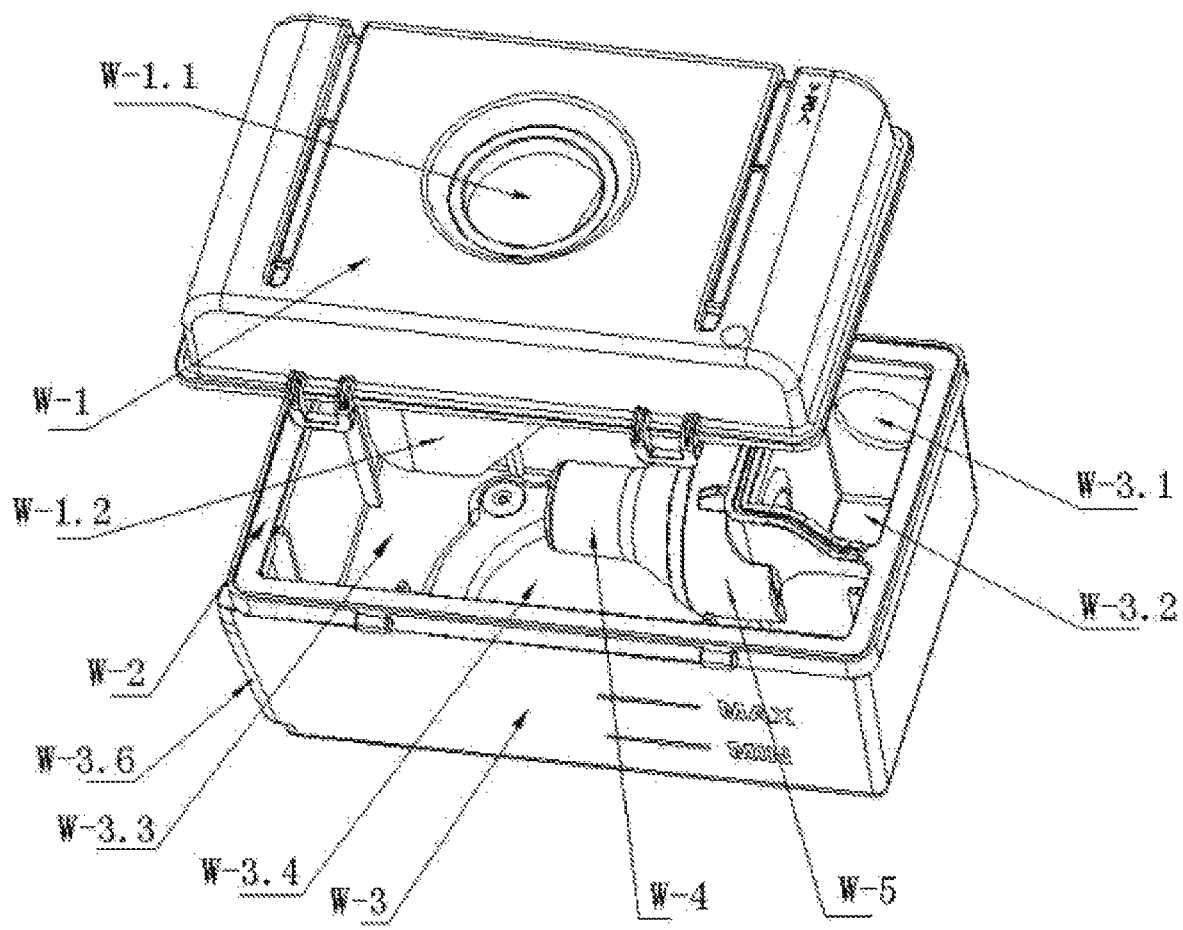
FIG. 12 is an axonometric drawing of an open condition of a water box according to the preferred embodiment of the present invention.
Figure 13:
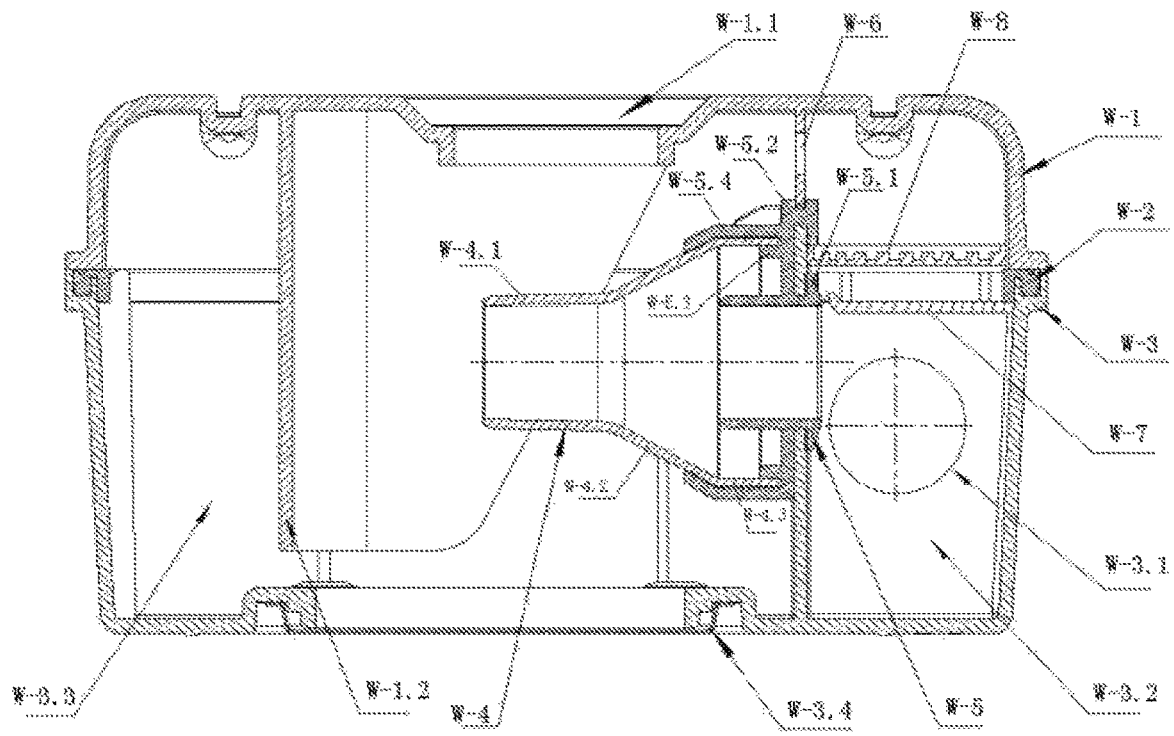
FIG. 13 is a main sectional view of the water box according to the preferred embodiment of the present invention.
Figure 14:
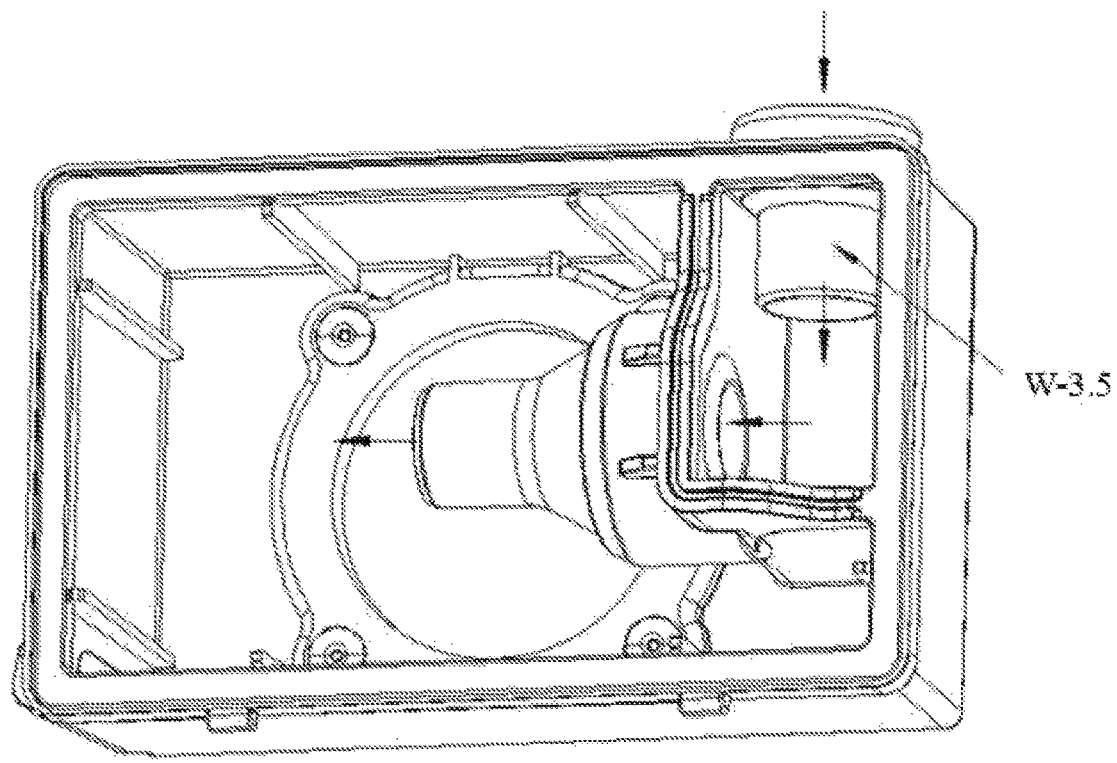
FIG. 14 is a three-dimensional sketch view of mounting of a silica gel air channel sleeve according to the preferred embodiment of the present invention.

As shown in FIGS. 12-14, a water box B' provided by the present invention, embodied as the heating and humidifying device, is realized as follows. The present invention provides an anti-backflow water box for the breathing machine, which is sealed and formed through a cooperation of an upper cover W-1 and a bottom box W-3, wherein: a bottom box flange is arranged in the bottom box W-3 for dividing the bottom box W-3 into a small chamber W-3.2 and a large chamber W-3.3; an upper cover flange is arranged at the upper cover W-1; when the upper cover cooperates with the bottom box, the upper cover flange correspondingly cooperates with the bottom box flange; a through-hole is provided on the bottom box flange; a silica gel funnel sleeve W-4 is fixedly arranged at the through-hole through a rubber sealing part W-5; the silica gel funnel sleeve W-4 comprises a small diameter section W-4.1, a large diameter section W-4.3 and a conical transition section W-4.2 between the small diameter section and the large diameter section; a heat conduction plate W-3.4 is arranged in the middle of a lower end face of the bottom box; an air inlet W-3.1 is provided at a side of the small chamber W-3.2; an air outlet W-1.1 is provided on the upper cover; the rubber sealing part W-5 comprises a hollow tube, and a first flange W-5.1 and a second flange W-5.2 are arranged around an end of the hollow tube; a distance between the first flange W-5.1 and the second flange W-5.2 cooperates with a thickness of the upper cover flange and the bottom box flange; an inner circular flange W-5.3 and an outer circular flange W-5.4 are arranged on the second flange W-5.2 with an interval; the large diameter section W-4.3 of the silica gel funnel sleeve W-4 is inserted into space between the inner circular flange W-5.3 and the outer circular flange W-5.4; a smallest height from a center hole at the small diameter section W-4.1 of the silica gel funnel sleeve W-4 to the lower end face of the bottom box is large than a height from a max line to the lower end face of the bottom box by 10-20 mm.

A U-shaped baffle W-1.2 is arranged at a lower end face of the upper cover W-1; a waterproof rubber gasket W-2 is arranged on an upper end face of the bottom box W-3 and the bottom box flange; the heat conduction plate W-3.4 is arranged in the middle of the lower end face of the bottom box W-3; a silica gel air channel sleeve W-3.5 is arranged at the air inlet W-3.1; the small chamber W-3.2 is interconnected with the large chamber W-3.3 through center holes of the rubber sealing part W-5 and the silica gel funnel sleeve W-4; the silica gel air channel sleeve W-3.5 is composed of a first part which is convex toward an interior of the small chamber W-3.2 and a second part which is convex toward an exterior of the small chamber W-3.2, wherein the second part is connected with an air outlet of a main body A' of the breathing machine, wherein all parts of the present invention except the water box is arranged in the main body; and, the silica gel air channel sleeve W-3.5 is convex toward the interior of the small chamber W-3.2 by 15-30 mm.

As shown in FIG. 12, two scale lines, respectively the max line and an min line, are marked on an outer side of the bottom box W-3, for indicating a water amount in the water box to a user; if a water level is above the max line, an anti-backflow function of the water box will lose efficacy; if the water level is below the min line, dry burning may occur, which affects a stable operation of the device. Thus, during the operation process, the water level in the water box should be between the min line and the max line.

Figure 15:
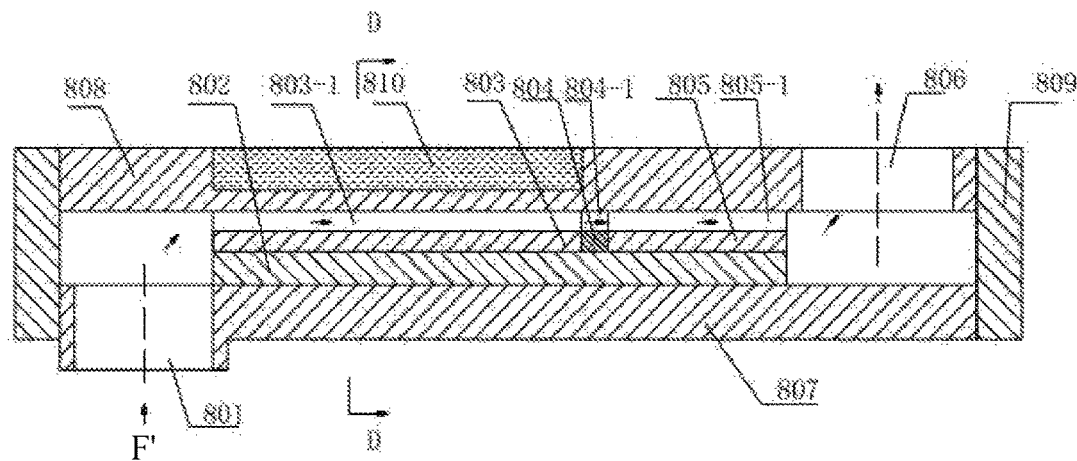
FIG. 15 is a first main sectional view of a passive heat and moisture exchanger (HME) in the water box according to the preferred embodiment of the present invention.
Figure 16:
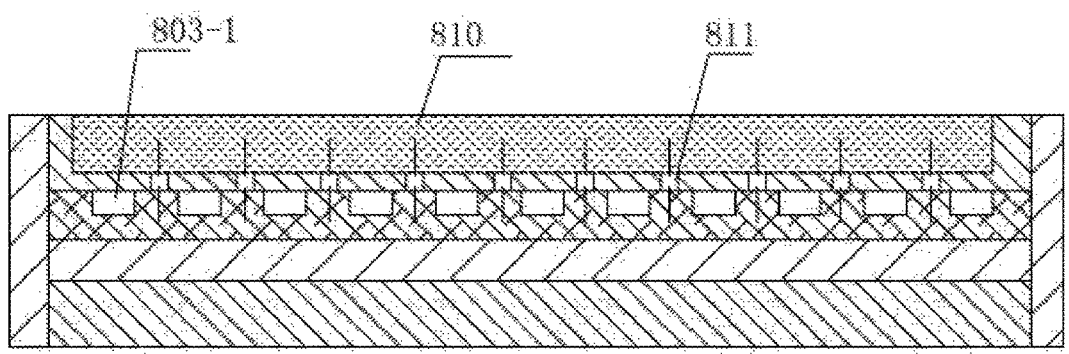
FIG. 16 is a D-D sectional view of the passive HME shown in FIG. 15.
Figure 17:
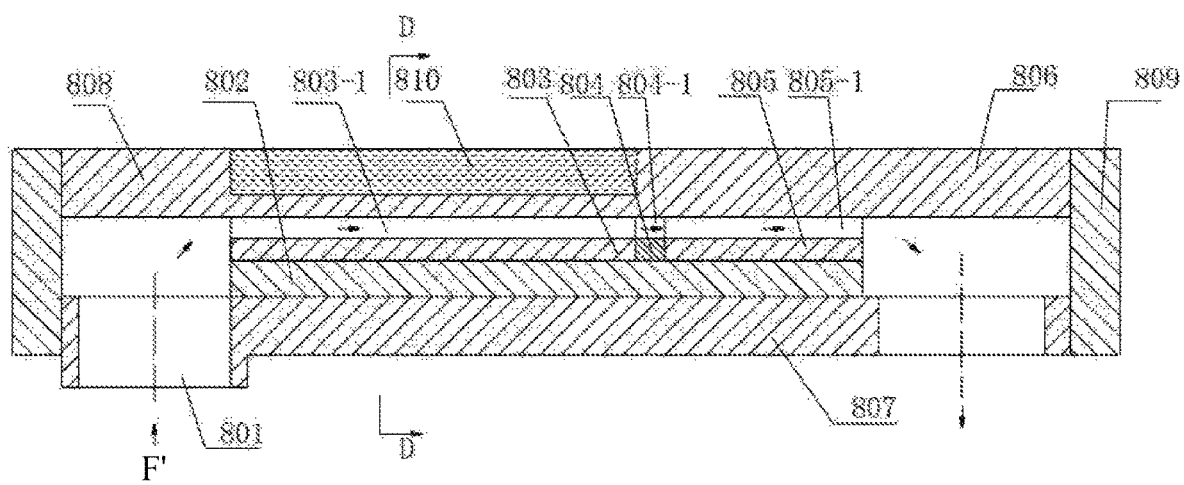
FIG. 17 is a second main sectional view of the passive HME according to the preferred embodiment of the present invention.

In order to combine a heat and moisture exchange function with the water box, the present invention provides an improved passive heat and moisture exchanger (HME) W-8. As shown in FIGS. 15-17, the passive HME W-8 comprises an exchanger bottom plate 807, an exchanger top plate 808 and a casing formed by exchanger side plates 809, wherein: an exchanger air inlet 801 is provided on the exchanger bottom plate 807; an exchanger air outlet 806 is provided on the exchanger top plate 808; an insulation plate 802 is arranged between the exchanger bottom plate 807 and the exchanger top plate 808; along an air pathway, an HME material plate 803, a sealing insulation strip 804 and an insulation heating plate 805 are successively arranged on the insulation plate 802; a plurality of first air channel grooves 803-1, second air channel grooves 804-1 and third air channel grooves 805-1 are respectively provided on the HME material plate 803, the insulation strip 804 and the insulation heating plate 805; positions of the HME material plate 803 and the insulation heating plate 805 are interchangeable; the first air channel grooves 803-1, the second air channel grooves 804-1 and the third air channel grooves 805-1 are interconnected with each other; a water tank 810 is arranged on the exchanger top plate 808 and is directly opposite to the HME material plate 803; multiple lines of interconnection holes 811 are provided at a bottom part of the water tank 810, which are directly opposite to protruding ribs of the HME material plate 803. Dry-cold air F' enters the exchanger through the exchanger air inlet 801, then brings moisture in HME material away through the plurality of first air channel grooves 803-1, and is heated through the third air channel grooves 805-1. Alternatively, the dry-cold air is firstly heated through the third air channel grooves 805-1, and then brings the moisture in the HME material away through the plurality of first air channel grooves 803-1. The heated and humidified gas is discharged out through the exchanger air outlet 806. The HME material plate 803 is made of heat-moisture retained material, wherein the heat-moisture retained material comprises moisture absorption foam and paper which have been processed with calcium salt or lithium salt, and other heat-moisture exchange materials.

A parallel connection of the passive HME W-8 with the water box is realized as follows. The passive HME W-8 is arranged at the upper cover W-1 in parallel and is directly opposite to the small chamber W-3.2, a rotational switch valve W-7 which rotates around a pivot is arranged in the small chamber W-3.2, and an opening W-6 is provided on a side wall which is in the middle of the upper cover W-1, so as to form a water box structure having an intelligent or selective heating and humidifying function.

A series connection of the passive HME W-8 with the water box is realized as follows. The passive HME W-8 is arranged at the upper cover W-1 in series and is directly opposite to the small chamber W-3.2, an end of the silica gel air channel sleeve W-3.5 is connected to the exchanger air inlet 801 through a flexible tube, and an air inlet of the rubber sealing part W-5 is connected to the exchanger air outlet 806 through a tube, so as to form a water box structure having a reinforced heating and humidifying function.

The anti-backflow function of the present invention is realized through following technical solutions. The waterproof rubber gasket W-2 is arranged on the upper end face of the bottom box W-3 for sealing and preventing water in the water box from flowing out of the water box during the operation process; a protruding part W-3.6 is arranged at a side edge of the bottom box W-3, so that it is convenient to observe the water level in the water box during the operation process and is easy to control the water amount in the water box; the heat conduction plate W-3.4 is arranged at the lower end face of the bottom box W-3, for heat conduction and insulation; during the operation process, a temperature of the heating plate is transmitted to the water box through the heat conduction plate W-3.4, so as to heat the water in the water box; the smallest height from the center hole at the small diameter section W-4.1 of the silica gel funnel sleeve W-4 to the lower end face of the bottom box W-3 is larger than the height from the max line to the lower end face of the bottom box W-3, so that when the water level is below the max line, no matter the position of the water box, water will not enter the silica gel funnel sleeve W-4, thereby realizing the omnidirectional anti-backflow function. The above structure realizes the primary anti-backflow function of the present invention. The rubber sealing part W-5 covers the whole large diameter section W-4.3 of the silica gel funnel sleeve W-4, so that even though a small amount of water enters the silica gel funnel sleeve W-4, the water will not directly enter the small chamber W-3.2, which assists the anti-backflow function. The first part of the silica gel air channel sleeve W-3.5, which is convex toward the interior of the small chamber W-3.2, avoids water flowing into the main body of the breathing machine when a small amount of water enters the small chamber W-3.2, and the above structure realizes the secondary anti-backflow function of the present invention. Meanwhile, the second part of the silica gel air channel sleeve W-3.5, which is convex toward the exterior of the small chamber W-3.2, is connected to the air outlet of the main body of the breathing machine, so that the gas discharged from the air outlet of the main body of the breathing machine will not be discharged sideways and all the gas enters the water box.

According to the present invention, the parallel connection of the passive HME W-8 which is able to automatically select a heating and humidifying pathway according to the humidity of the inlet gas is realized as follows. The control device determines according to the air humidity measured by a sensor at the silica gel air channel sleeve W-3.5. If the humidity collected by a temperature and humidity sensor 112 is lower than a rated value such as 35%, the control device upward rotates the switch valve W-7, so as to block the exchanger air inlet of the passive HME W-8; the gas enters the small chamber W-3.2 through the air inlet W-3.1, then enters the large chamber W-3.3 through the center holes of the rubber sealing part W-5 and the silica gel funnel sleeve W-4; when the gas goes out of the center hole of the small diameter section W-4.1 of the silica gel funnel sleeve W-4, the gas will be blocked by the U-shaped baffle W-1.2 of the upper cover W-1, causing the rebound, so that the gas will stay in the water box for a certain time; meanwhile, the heating plate heats the water in the water box through the heat conduction plate W-3.4, so that the retained gas will be heated and humidified; then the heated and humidified gas is discharged out from the air outlet W-1.1 of the upper cover W-1, thereby finishing the active heat and moisture exchange function. If the humidity is larger than the rated value such as 35%, the control device downward rotates the switch valve W-7, so as to block the air inlet of the rubber sealing part W-5; the gas enters the small chamber W-3.2 through the air inlet W-3.1, then enters the parallel HME W-8 through the exchanger air inlet 801 and finishes the heat and moisture exchange therein, thereafter is discharged out from the exchanger air outlet 806 and blown out through the opening W-6 and the air outlet W-1.1, thereby finishing the passive heat and moisture exchange function.

According to the present invention, the series connection of the passive HME W-8 which is able to automatically select the heating and humidifying pathway according to the humidity of the inlet gas is realized as follows. The gas enters the small chamber W-3.2 through the air inlet W-3.1, then enters the parallel passive HME W-8 through the exchanger air inlet 801 and finishes the heat and moisture exchange therein, thereafter is discharged out from the exchanger air outlet 806 and enters the large chamber W-3.3 through the center holes of the rubber sealing part W-5 and the silica gel funnel sleeve W-4; when the gas leaves out from the center hole of the small diameter section W-4.1 of the silica gel funnel sleeve W-4, the gas will be blocked by the U-shaped baffle W-1.2 of the upper cover W-1, causing the rebound, so that the gas will stay in the water box for a certain time; at the same time, the heating plate heats the water in the water box through the heat conduction plate W-3.4, and thus the retained gas is heated and humidified; the heated and humidified gas is blown out through the air outlet W-1.1 of the upper cover W-1, thereby finishing the active heat and moisture exchange function with the series connection of the passive HME W-8.

The anti-backflow structure of the water box provided by the present invention has following beneficial effects. The waterproof rubber gasket is arranged on the upper end face of the bottom box for sealing and preventing the water in the water box from flowing out of the water box during the operation process; the protruding part is arranged at the side edge of the bottom box, so that it is convenient to observe the water level in the water box during the operation process and is easy to control the water amount in the water box; the heat conduction plate is arranged at the lower end face of the bottom box, for heat conduction and insulation; during the operation process, the temperature of the heating plate is transmitted to the water box through the heat conduction plate, so as to heat the water in the water box; the smallest height from the center hole at the small diameter section of the silica gel funnel sleeve to the lower end face of the bottom box is larger than the height from the max line to the lower end face of the bottom box by 10-20 mm, so that when the water level is below the max line, no matter the position of the water box, water will not enter the silica gel funnel sleeve, thereby realizing the omnidirectional anti-backflow function. The above structure realizes the primary anti-backflow function of the present invention. The rubber sealing part covers the whole large diameter section of the silica gel funnel sleeve, so that even though a small amount of water enters the silica gel funnel sleeve, the water will not directly enter the small chamber, which assists the anti-backflow function. The first part of the silica gel air channel sleeve, which is convex toward the interior of the small chamber, avoids the water flowing into the main body of the breathing machine when a small amount of water enters the small chamber, and the above structure realizes the secondary anti-backflow function of the present invention. Meanwhile, the second part of the silica gel air channel sleeve, which is convex toward the exterior of the small chamber, is connected to the air outlet of the main body of the breathing machine, so that the gas discharged from the air outlet of the main body of the breathing machine will not be discharged sideways and all the gas enters the water box.

According to the present invention, the water box structure which automatically selects the heating and humidifying pathway according to the humidity of the inlet gas has following technical effects.

1) According to the air humidity, two humidifying pathways can be selected which have the different heating and humidifying effects. The first one is a pathway only from the passive HME to the air outlet; and the second one is a pathway only from space above the water in the large chamber of the water box to the air outlet.

2) The reinforced heating and humidifying structure which is realized through the series connection of the passive HME and the large chamber of the water box has an obvious effect and will make the patients having a good feeling in the upper respiratory tract.

The above anti-backflow structure design and the heating and humidifying structure design support each other functionally. Only when the anti-backflow function is realized, the heating and humidifying function can continuously play the role. The heating and humidifying structure tightly cooperates with the anti-backflow structure of the large and small chambers. The design of the large and small chambers is established based on the parallel connection or series connection of the passive HME and the large chamber of the water box. The structure of the water box provided by the present invention is obtained through the cooperation of the above two structure designs.

The basic principles, main features and advantages of the present invention are showed and described above. One skilled in the art should understand that the present invention is not limited by the above preferred embodiment, and the preferred embodiment and the specification is only for describing the principles of the present invention. The various modifications and improvements encompassed within the spirit and scope of the present invention are included in the protection scope of the present invention. The protection scope of the present invention is limited by the following claims and equivalents thereof.

What is claimed is:

1. A portable breathing machine, comprising a body case (100), wherein: a fan box (101), a heating and humidifying device (106), a cut-off device (108) and a control device (113) are arranged in the body case (100); a fan (8) is arranged in the fan box (101) through a fan noise reduction device (102); an air outlet of the fan box (101) is connected with an internal breathing tube (107); the cut-off device (108) is arranged on the internal breathing tube (107); an air outlet of the cut-off device (108) is connected to the heating and humidifying device (106) through the internal breathing tube (107); and an air outlet of the heating and humidifying device (106) is connected to an external breathing tube (104) and a mask (105);

the fan noise reduction device (102) comprises a lower flexible cover (3) and an upper flexible cover (5), wherein: the lower flexible cover cooperates with the upper flexible cover to from an enclosed cavity for containing the fan (8); the fan (8) hangs from the upper flexible cover (5) through a plurality of flexible hanging columns (6);

an enclosed S-shaped air channel (3-1) and a fan air inlet channel (3-2) which are successively connected are integrated at the fan noise reduction device (102), wherein: an S-shaped air channel groove is provided at a bottom part of the lower flexible cover (3) of the fan noise reduction device (102); after assembling, the enclosed S-shaped air channel (3-1) is formed between the lower flexible cover (3) and the fan box (101);

the fan air inlet channel (3-2) comprises a hole channel (13), an ascending channel (3-2.1) and a descending channel (3-2.2), wherein: the ascending channel (3-2.1) is formed by a through-hole which extends from the bottom to the top of the fan (8); an exit of the ascending channel (3-2.1) is located at an upper part of the enclosed cavity; the hole channel (13) is provided at a bottom side wall of the through-hole; the hole channel (13) is interconnected with the enclosed S-shaped air channel (3-1) and the ascending channel (3-2.1); the descending channel (3-2.2) is formed from the bottom to the top of the fan (8) in the enclosed cavity; after passing through the enclosed S-shaped air channel (3-1), gas passes through the hole channel (13) at a tail end of the enclosed S-shaped air channel (3-1) and enters the ascending channel (3-2.1), then gas reaches the upper part of the enclosed cavity after leaving from the exit of the ascending channel (3-2.1), and finally gas descends to a fan air inlet (12) at a bottom part of the fan (8) through the descending channel (3-2.2) around the fan (8);

the heating and humidifying device (106) is formed through a cooperation of an upper cover (W-1) and a bottom box (W-3); a bottom box flange is arranged in the bottom box (W-3) for dividing the bottom box (W-3) into a small chamber (W-3.2) and a large chamber (W-3.3); an upper cover flange is arranged at the upper cover (W-1); when the upper cover cooperates with the bottom box, the upper cover flange correspondingly cooperates with the bottom box flange; a through-hole is provided on the bottom box flange; a silica gel funnel sleeve (W-4) is fixedly arranged at the through-hole through a rubber sealing part (W-5); the silica gel funnel sleeve (W-4) comprises a small diameter section (W-4.1), a large diameter section (W-4.3) and a conical transition section (W-4.2) between the small diameter section and the large diameter section; a heat conduction plate (W-3.4) is arranged in the middle of a lower end face of the bottom box; an air inlet (W-3.1) is provided at a side of the small chamber (W-3.2), an air outlet (W-1.1) is provided on the upper cover; the rubber sealing part (W-5) comprises a hollow tube, and a first flange (W-5.1) and a second flange (W-5.2) are arranged around an end of the hollow tube; a distance between the first flange (W-5.1) and the second flange (W-5.2) cooperates with a thickness of the upper cover flange and the bottom box flange; an inner circular flange (W-5.3) and an outer circular flange (W-5.4) are arranged on the second flange (W-5.2) with an interval; the large diameter section (W-4.3) of the silica gel funnel sleeve (W-4) is inserted into space between the inner circular flange (W-5.3) and the outer circular flange (W-5.4); a smallest height from a center hole at the small diameter section (W-4.1) of the silica gel funnel sleeve (W-4) to the lower end face of the bottom box is larger than a height from a max line to the lower end face of the bottom box by 10-20 mm.

2. The portable breathing machine, as recited in claim 1, wherein: the fan box (101) comprises a bottom fan box (1) and a top fan box (4); a bottom fan box damping piece (2) is arranged between the bottom fan box (1) and the lower flexible cover (3); and a top fan box damping piece (7) is arranged between the top fan box (4) and the upper flexible cover (5).

3. The portable breathing machine, as recited in claim 1, further comprising an air channel structure further comprising a fan air outlet channel arranged at a fan air outlet (11); the fan air outlet channel comprises a flexible connection tube (9) arranged at the fan air outlet (11); the flexible connection tube (9) is connected with an elbow connection tube (10); and the elbow connection tube (10) is connected with the internal breathing tube (107).

4. The portable breathing machine, as recited in claim wherein: the enclosed S-shaped air channel (3-1) and the fan air inlet channel (3-2) are made through a mould before shaping the upper flexible cover and the lower flexible cover (3), and thereafter the upper flexible cover and the lower flexible cover are integrated together.

5. The portable breathing machine, as recited in claim 1, wherein: the enclosed S-shaped air channel (3-1) is divided into a first quadrant and a second quadrant, defined by an axis running through the fan (8) and the bottom part of the lower flexible cover (3); an air inlet of the enclosed S-shaped air channel is provided at a bottom of a side wall in the second quadrant of the lower flexible cover (3), which is directly opposite to an air inlet of the fan box (101); and the enclosed S-shaped air channel (3-1) at the bottom part of the lower flexible cover (3) at least comprises a first sinuous section (3-1.1) and a straight section (3-1.4) following a last sinuous section, which are successively connected; the first sinuous section (3-1.1) is formed through firstly going straight from the air inlet of the enclosed S-shaped air channel for 40-60 mm at an angle of −90°, then going straight for 10-20 mm at an angle of 0°, and going straight for 40-60 mm at an angle of 90°; the first sinuous section (3-1.1) is connected with the straight section (3-1.4).

6. The portable breathing machine, as recited in claim 5, wherein: the enclosed S-shaped air channel (3-1) further comprises a second sinuous section (3-1.2); the second sinuous section is formed through going straight from a tail end of the first sinuous section (3-1.1) for 10-20 mm at an angle of 0° and then going straight for 40-60 mm at an angle of −90°, then going straight for 40-60 mm at an angle of 90° of the first sinuous section; a tail end of the second sinuous section (3-1.2) is connected with the straight section (3-1.4).

7. The portable breathing machine, as recited in claim 6, wherein: the enclosed S-shaped air channel (3-1) further comprises a third sinuous section (3-1.3); the third sinuous section (3-1.3) is formed through going straight from the tail end of the second sinuous section (3-1.2) for 10-20 mm at an angle of 0° and then going straight for 40-60 mm at an angle of 90°, then going straight for 40-60 mm at an angle of −90° of the second sinuous section; a tail end of the third sinuous section is connected with the straight section (3-1.4).

8. The portable breathing machine, as recited in claim 1, wherein: the enclosed S-shaped air channel (3-1) has a pathway of a smooth curve and comprises at least one sinuous section.

9. The portable breathing machine, as recited in claim 1, wherein: each flexible hanging column (6) comprises a hanging column body and a flange arranged at an end of the hanging column body; a clamping groove is provided on the hanging column body; the flexible hanging column (6) hangs from a hanging hole of the upper flexible cover (5) through the flange; at least three clamping holes are provided on the fan (8); the fan (8) is fixedly connected with the clamping grooves of the flexible hanging columns (6) through the clamping holes; the clamping groove of each hanging column body is a thread groove; and the flexible hanging columns (6) further fix the fan (8) through a cooperation of flexible clamping nuts and the clamping grooves of the hanging column bodies.

10. The portable breathing machine, as recited in claim 1, wherein: the flexible hanging column (6) comprises a metal reinforced frame; and the metal reinforce frame is integrated with rubber and ethylene-vinyl acetate (EVA) material through injection molding.

11. The portable breathing machine, as recited in claim 1, wherein: the cut-off device (108) comprises a rectifying frame (J-1), a honeycomb rectifying part (J-2), a connection duct (J-3), a flexible sleeve (J-4), an external connection tube (J-5), a silica gel connection part (J-6) and a sensor unit (J-7); the connection duct (J-3) is a tubular part whose left end serves as an air inlet and right end serves as an air outlet; the air inlet is connected with the rectifying frame (J-1); the air outlet is inserted into a groove of the flexible sleeve (J-4); the external connection tube (J-5) is inserted into an inner hole of the flexible sleeve (J-4); cut-off columns (J-3.1, J-3.2 and J-3.3) are arranged on the connection duct (J-3) with an interval and have a certain distance from a center line; inner holes of the connection duct (0.1-3) are respectively interconnected with inner holes of the cut-off columns (J-3.1, J-3.2 and J-3.3); the cut-off columns (J-3.1, J-3.2 and J-3.3) of the connection duct (J-3) are connected with the silica gel connection part (J-6); the silica gel connection part (0.1-6) is connected with the sensor unit (J-7); and the honeycomb rectifying part (J-2) is arranged between the connection duct (J-3) and the rectifying frame (J-1).

12. The portable breathing machine, as recited in claim 11, wherein the cut-off columns (J-3.1, J-3.2 and J-3.3) comprises a first cut-off column (J-3.1), a second cut-off column (J-3.2) and a third cut-off column (J-3.3); the silica gel connection part (J-6) has a first connection through-hole (J-6.1), a second connection through-hole (J-6.2) and a third connection through-hole (J-6.3) thereon with a same interval as that of the cut-off columns (J-3.1, J-3.2 and J-3.3); the sensor unit (J-7) comprises a before-rectifying flow sensor (J-7.1), an after-rectifying flow sensor (J-7.2) and an after-rectifying pressure sensor (J-7.3); air inlet ends of the first connection through-hole (J-6.1), the second connection through-hole (J-6.2) and the third connection through-hole (J-6.3) are respectively inserted into the corresponding first cut-off column (J-3.1), the second cut-off column (J-3.2) and the third cut-off column (J-3.3) of the connection duct (J-3); the before-rectifying flow sensor (J-7.1), the after-rectifying flow sensor (J-7.2) and the after-rectifying pressure sensor (J-7.3) are respectively arranged at air outlet ends of the first connection through-hole (J-6.1), the second connection through-hole (J-6.2) and the third connection through-hole (J-6.3).

13. The portable breathing machine, as recited in claim 11, wherein: the rectifying frame (J-1) comprises a cover body (J-1.1) and a fastening part (J-1.2) arranged inside the cover body (J-1.1); a top part of the cover body (J-1.1) has an opening; a cross (J-1.3) is arranged above the opening; an inner circumference surface of the cover body (J-1.1) has a cover body connection part (J-1.4); a cut-off ring (J-3.4) is arranged at an inner side of the air inlet of the connection duct (J-3); an inner fastening part (J-3.5) is arranged on the cut-off ring (J-3.4); and, a connection part (J-3.7) and an outer fastening part (J-3.6) are arranged at an outer side of the air inlet of the connection duct (J-3).

14. The portable breathing machine, as recited in claim 13, wherein: the honeycomb rectifying part (J-2) has a plurality of honeycomb-shaped holes (J-2.1) which are adjacent to each other, an upper end face fixing groove (J-2.2) and a lower end face fixing groove (J-2.3) thereon; an outer circumference surface of the honeycomb rectifying part (J-2) cooperates with an inner circumference surface of the connection duct (J-3); the inner fastening part (J-3.5) is fastened at a bottom part of the lower end face fixing groove (J-2.3); the cover body connection part (J-1.4) of the rectifying frame (J-1) is fixedly connected with the connection part (J-3.7) of the connection duct (J-3); when the cover body connection part (J-1.4) is fastened with the outer fastening part (J-3.6) of the connection duct (J-3), the fastening part (J-1.2) of the rectifying frame (J-1) is inserted into and stopped at a bottom part of the upper end face fixing groove (J-2.2).

15. The portable breathing machine, as recited in claim 1; wherein: a U-shaped baffle (W-1.2) is arranged at a lower end face of the upper cover (W-1); a U-shaped concave section of the U-shaped baffle (W-1.2) is directly opposite to the small diameter section (W-4.1) of the silica gel funnel sleeve (W-4); a silica gel air channel sleeve (W-3.5) is arranged at the air inlet; the silica gel air channel sleeve (W-3.5) is convex toward an interior of the small chamber (W-3.2) by 15-30 mm; a waterproof rubber gasket (W-2) is arranged on an upper end face of the bottom box and the bottom box flange.

16. The portable breathing machine, as recited in claim 15, wherein: a passive heat and moisture exchanger (WE) (W-8) is arranged above the small chamber (W-3.2) in parallel; a rotational switch valve (W-7) which rotates around a pivot is arranged in the small chamber (W-3.2); and an opening is provided on a side wall which is in the middle of the upper cover (W-1).

17. The portable breathing machine, as recited in claim 15, wherein: a passive HME (W-8) is arranged above the small chamber (W-3.2) in series; an end of the silica gel air channel sleeve (W-3.5) is connected to an exchanger air inlet (801) through a flexible tube; an air inlet of the rubber sealing part (W-5) is connected to an exchanger air outlet (806) through a tube.

18. The portable breathing machine, as recited in claim 17, wherein: the passive HME (W-8) comprises an exchanger bottom plate (807), an exchanger top plate (808) and a casing formed by exchanger side plates (809); the exchanger air inlet (801) is provided on the exchanger bottom plate (807); the exchanger air outlet (806) is provided on the exchanger top plate (808) or the exchanger bottom plate (807); an insulation plate (802) is arranged between the exchanger bottom plate (807) and the exchanger top plate (808); an HME material plate (803), a sealing insulation strip (804) and an insulation heating plate (805) are successively arranged on the insulation plate (802); a plurality of first air channel grooves (803-1), second air channel grooves (804-1) and third air channel grooves (805-1) are respectively provided on the HME material plate (803), the sealing insulation strip (804) and the insulation heating plate (805); the first air channel grooves (803-1), the second air channel grooves (804-1) and the third air channel grooves (805-1) are successively interconnected; a water tank (810) is arranged on the exchanger top plate (808) and is directly opposite to the HME material plate (803); multiple lines of interconnection holes (811) are provided on a bottom part of the water tank (810); the interconnection holes (811) are directly opposite to protruding ribs among the plurality of first air channel grooves (803-1) on the HME material plate (803).

* * * * *